US012310661B2

United States Patent
Draelos et al.

(10) Patent No.: US 12,310,661 B2
(45) Date of Patent: May 27, 2025

(54) SYSTEMS AND METHODS FOR IMAGING A TARGET FEATURE OF A SUBJECT BASED ON TRACKED POSITIONS OF THE SUBJECT AND THE TARGET FEATURE

(71) Applicant: Duke University, Durham, NC (US)

(72) Inventors: Mark Draelos, Durham, NC (US); Joseph Izatt, Durham, NC (US); Anthony Kuo, Durham, NC (US); Pablo Ortiz, Durham, NC (US); Ryan McNabb, Durham, NC (US)

(73) Assignee: Duke University, Durham, NC (US)

( * ) Notice: Subject to any disclaimer, the term of this patent is extended or adjusted under 35 U.S.C. 154(b) by 820 days.

(21) Appl. No.: 17/413,996

(22) PCT Filed: Jan. 29, 2020

(86) PCT No.: PCT/US2020/015598
§ 371 (c)(1),
(2) Date: Jun. 15, 2021

(87) PCT Pub. No.: WO2020/160097
PCT Pub. Date: Aug. 6, 2020

(65) Prior Publication Data
US 2022/0039648 A1    Feb. 10, 2022

Related U.S. Application Data

(60) Provisional application No. 62/798,052, filed on Jan. 29, 2019.

(51) Int. Cl.
*A61B 3/00* (2006.01)
*A61B 3/02* (2006.01)
(Continued)

(52) U.S. Cl.
CPC ............ *A61B 3/102* (2013.01); *A61B 3/0033* (2013.01); *A61B 3/113* (2013.01); *A61B 3/117* (2013.01); *A61B 3/12* (2013.01); *A61B 3/14* (2013.01)

(58) Field of Classification Search
CPC ......... A61B 3/02; A61B 3/102; A61B 3/1025; A61B 3/0075; A61B 3/113; A61B 3/1015; A61B 3/1225; A61B 3/024; A61B 3/005
(Continued)

(56) References Cited

U.S. PATENT DOCUMENTS

| 5,164,827 A | 11/1992 | Paff |
| 2007/0252951 A1* | 11/2007 | Hammer ................ G01S 17/66 351/221 |

(Continued)

OTHER PUBLICATIONS

Huang, D. et al, "Optical Coherence Tomography," Science, Nov. 1991, 1178-1181, 254(5035), Springer, New York. (12 pages).
(Continued)

*Primary Examiner* — Dawayne Pinkney
(74) *Attorney, Agent, or Firm* — Olive Law Group, PLLC

(57) ABSTRACT

Systems and methods for imaging a target feature of a subject based on the tracked positions of the subject and the target feature are disclosed. According to an aspect, a system includes a scanner configured to image a target feature of a subject. The system includes a mechanism configured to move the scanner. Further, the system includes a subject tracker configured to track positioning of the subject. The system includes a feature tracker configured to track positioning of the target feature. A controller is configured to control the mechanism to move the feature tracker to a position such that the feature tracker is operable to track a position of the target feature. The controller controls the mechanism to move the scanner to a position such that the
(Continued)

scanner is operable to image the target feature based on the tracked position of the target feature by the feature tracker.

15 Claims, 37 Drawing Sheets

(51) Int. Cl.
| | |
|---|---|
| A61B 3/10 | (2006.01) |
| A61B 3/113 | (2006.01) |
| A61B 3/117 | (2006.01) |
| A61B 3/12 | (2006.01) |
| A61B 3/14 | (2006.01) |

(58) Field of Classification Search
USPC ........ 351/200, 205, 206, 208–210, 221–223, 351/245–246
See application file for complete search history.

(56) References Cited

U.S. PATENT DOCUMENTS

| | | | |
|---|---|---|---|
| 2012/0200689 | A1 | 8/2012 | Friedman et al. |
| 2014/0022270 | A1* | 1/2014 | Rice-Jones .............. A61B 3/12 345/589 |
| 2015/0342460 | A1 | 12/2015 | Izatt et al. |
| 2016/0338589 | A1 | 11/2016 | Carrasco-Zevallos et al. |
| 2017/0071466 | A1* | 3/2017 | Kowal ................. A61B 3/0075 |
| 2017/0215733 | A1* | 8/2017 | Mak ................... A61B 17/0206 |
| 2018/0028355 | A1* | 2/2018 | Raksi ....................... A61B 3/13 |
| 2020/0085292 | A1* | 3/2020 | Fukuma ............... A61B 3/0025 |
| 2021/0100448 | A1* | 4/2021 | Hurst ......................... G06T 5/70 |

OTHER PUBLICATIONS

Retina/Vitreous Preferred Practice Pattern Panel, "Diabetic Retinopathy Preferred Practice Pattern," 2019, p. 66-p. 145, American Academy of Ophthalmology, San Francisco. (80 pages).

Izatt, J.A. et al., "Micrometer-Scale Resolution Imaging of the Anterior Eye In Vivo With Optical Coherence Tomography," Arch Ophthalmol, Dec. 1994, 1584-1589, 112, American Medical Association, Chicago. (6 pages).

Cornea/External Disease Preferred Practice Pattern Panel, "Corneal Edema and Opacification Preferred Practice Pattern," 2018, p. 216-p. 285, American Academy of Ophthalmology, San Francisco. (70 pages).

Hee, M.R. et al., "Optical Coherence Tomography of the Human Retina," Arch Ophthalmol. Mar. 1995, 325-332, 113, American Medical Association, Chicago. (8 pages).

Walker, M.C. et al., "Neurological examination of the unconscious patient," Journal of the Royal Society of Medicine, Jul. 1999, 353-355, 92, Sage Publishing, Thousand Oaks. (3 pages).

Baltrusaitis, T. et al., "OpenFace 2.0: Facial Behavior Analysis Toolkit," 13th IEEE International Conference on Automatic Face & Gesture Recognition, 2018, 59-66, IEEE, New York City. (8 pages).

Puliafito, C.A. et al., "Imaging of Macular Diseases with Optical Coherence Tomography," Ophthalmology, Feb. 1995, 217-229, Elsevier, Amsterdam. (13 pages).

Radhakrishnan, S. et al., "Real-Time Optical Coherence Tomography of the Anterior Segment at 1310 nm," Arch Ophthalmol, Aug. 2001, 1179-1185, 119, American Medical Association, Chicago. (7 pages).

Carrasco-Zevallos, O. et al., "Pupil tracking optical coherence tomography for precise control of pupil entry position," Biomedical Optics Express, Sep. 2015, 3405-3419, 6(9), OSA, Washington, D.C. (15 pages).

Retina/Vitreous Preferred Practice Pattern Panel, "Age-Related Macular Degeneration Preferred Practice Pattern," 2019, p. 1-p. 65, American Academy of Ophthalmology, San Francisco. (65 pages).

Jung, W. et al., "Handheld Optical Coherence Tomography Scanner for Primary Care Diagnostics," IEEE Transactions on Biomedical Engineering, Mar. 2011, 741-744, 58(3), IEEE, New York City. (4 pages).

Schmidt-Erfurth, U. et al., "A view of the current and future role of optical coherence tomography in the management of age-related macular degeneration," Eye, 2017, 26-44, 31, Springer Nature, Heidelberg, Germany. (19 pages).

Lu, C.D. et al., "Handheld ultrahigh speed swept source optical coherence tomography instrument using a MEMS scanning mirror," Biomedical Optics Express, Jan. 2014, 293-311, 5(1), OSA, Washington, D.C. (19 pages).

Nankivil, D. et al., "Handheld, rapidly switchable, anterior/posterior segment swept source optical coherence tomography probe," Biomedical Optics Express, Nov. 2015, 4516-4528, 6(11), OSA, Washington, D.C. (13 pages).

Yang, J. et al., "Handheld optical coherence tomography angiography," Biomedical Optics Express, Apr. 2017, 2287-2300, 8(4), OSA, Washington, D.C. (14 pages).

Larocca, F. et al., "In vivo cellular-resolution retinal imaging in infants and children using an ultracompact handheld probe," Nature Photonics, Sep. 2016, 580-585, 10, Springer Nature, Heidelberg, Germany. (6 pages).

Ricco, S. et al., "Correcting Motion Artifacts in Retinal Spectral Domain Optical Coherence Tomography via Image Registration," MICCAI, 2009, 100-107, 5761, Springer-Verlag, Heidelberg. (8 pages).

Kraus, M.F. et al., "Motion correction in optical coherence tomography volumes on a per A-scan basis using orthogonal scan patterns," Biomedical Optics Express, Jun. 2012, 1182-1199, 3(6), OSA, Washington, D.C. (18 pages).

Capps, A.G. et al., "Correction of eye-motion artifacts in AO-OCT data sets," Proceedings of SPIE, 2011, 78850D-1-78850D-7, 7885, SPIE, Bellingham. (8 pages).

Garrido-Jurado, S. et al., "Automatic generation and detection of highly reliable fiducial markers under occlusion," Pattern Recognition, 2014, 2280-2292, 47, Elsevier, Amsterdam. (13 pages).

Zadeh, A., "Convulational Experts Constrained Local Model for 3D Facial Landmark Detection," IEEE International Conference on Computer Vision Workshops, 2017, 2519-2528, IEEE, New York City. (10 pages).

Spaide, R.F. et al., "Image Artifacts in Optical Coherence Tomography Angiography," Retina, 2015, 2163-2180, 35(11), Ophthalmic Communications Society, Inc., Villanova. (18 pages).

Song, S. et al., "Development of a clinical prototype of a miniature hand-held optical coherence tomography probe for prematurity and pediatric ophthalmic imaging," Biomedical Optics Express, May 2019, 2383-2398, 10(5), OSA, Washington, D.C. (16 pages).

Loo, J. et al., "Deep longitudinal transfer learning-based automatic segmentation of photoreceptor ellipsoid zone defects on optical coherence tomography images of macular telangiectasia type 2," Biomedical Optics Express, Jun. 2018, 2681-2698, 9(6), OSA, Washington, D.C. (18 pages).

Dos Santos, V.A. et al., "CorneaNet: fast segmentation of cornea OCT scans of healthy and keratoconic eyes using deep learning," Biomedical Optics Express, Feb. 2019, 622-641, 10(2), OSA, Washington, D.C. (20 pages).

De Fauw, J. et al., "Clinically applicable deep learning for diagnosis and referral in retinal disease," Nature Medicine, Sep. 2018, 1342-1350, 24, Springer Nature, New York. (15 pages).

Lu, W. et al., "Deep Learning-Based Automated Classification of Multi-Categorical Abnormalities From Optical Coherence Tomography Images," TVST, Dec. 2018, 1-10, 7(6), ARVO Journals, Rockville. (10 pages).

Bruce, B.B. et al., "Nonmydriatic Ocular Fundus Photography in the Emergency Department," The New England Journal of Medicine, Jan. 2011, 387-389, 364(4), Massachusetts Medical Society, Waltham. (3 pages).

Asaoka, R. et al., "Using Deep Learning and Transfer Learning to Accurately Diagnose Early-Onset Glaucoma From Macular Optical Coherence Tomography Images," Am J Ophthalmol, Feb. 2019, 136-145, 198, Elsevier, Amsterdam. (10 pages).

(56) References Cited

OTHER PUBLICATIONS

Van Buskirk, E.M. et al., "The Anatomy of the Limbus," Eye, 1989, 101-108, 3. (8 pages).
Drexler, W. et al., "Optical coherence tomography today: speed, contrast, and multimodality," Journal of Biomedical Optics, Jul. 2014, 071412-1-071412-34, 19(7), SPIE, Bellingham. (35 pages).
Bruce, B.B. et al., "Feasibility of Nonmydriatic Ocular Fundus Photography in the Emergency Department: Phase I of the FOTO-ED Study," Academic Emergency Medicine, Sep. 2011, 928-933, 18(9), Society for Academic Emergency Medicine, Ses Plaines. (6 pages).
Maclachlan, C. et al., "Normal values and standard deviations for pupil diameter and interpupillary distance in subjects aged 1 month to 19 years," Ophthal. Physiol. Opt., 2002, 175-182, 22, The College of Optometrists, London, United Kingdom. (8 pages).
Goebel, W. et al., "Retinal Thickness in Diabetic Retinopathy: A Study Using Optical Coherence Tomography (OCT)," Retina, 2002, 759-767, 22(6), Ophthalmic Communications Society, Inc., Villanova. (9 pages).
Fotedar, R. et al., "Distribution of Axial Length and Ocular Biometry Measured Using Partial Coherence Laser Interferometry (IOL Master) in an Older White Population," Ophthalmology, 2010, 417-423, 117, Elsevier, Amsterdam. (7 pages).
Lam, A.K.C. et al., "The repeatability and accuracy of axial length and anterior chamber depth measurements from the IOLMasterTM," Ophthal. Physiol. Opt., 2001, 477-483, 21(6), Elsevier, Amsterdam. (7 pages).
Randleman, J.B. et al., "Comparison of central and peripheral corneal thickness measurements with scanning-slit, Scheimpflug and Fourier-domain ocular coherence tomography," Br J Ophthalmol, 2015, 1176-1181, 99, BMJ, London, United Kingdom. (6 pages).
Buehl, W. et al., "Comparison of Three Methods of Measuring Corneal Thickness and Anterior Chamber Depth," American Journal of Ophthalmology, Jan. 2006, 7-12.e1, 141(1), Elsevier, Amsterdam. (7 pages).
La Rosa, F.A. et al., "Central Corneal Thickness of Caucasians and African Americans in Glaucomatous and Nonglaucomatous Populations," Arch Ophthalmol, Jan. 2001, 23-27, 119, American Medical Association, Chicago. (5 pages).
Herndon, L.W. et al., "Central Corneal Thickness in Normal, Glaucomatous, and Ocular Hypertensive Eyes," Arch Ophthalmol, Sep. 1997, 1137-1141, 115, American Medical Association, Chicago. (5 pages).
Alamouti, B. et al., "Retinal thickness decreases with age: an OCT study," Br J Ophthalmol, 2003, 899-901, 87, BMJ, London, United Kingdom. (3 pages).
Viehland, C. et al., "Enhanced volumetric visualization for real time 4D intraoperative ophthalmic swept-source OCT," Biomedical Optics Express, May 2016, 1815-1829, 7(5), OSA, Washington, D.C. (15 pages).
Escudero-Sanz, I. et al., "Off-axis aberrations of a wide-angle schematic eye model," J. Opt. Soc. Am. A, Aug. 1999, 1881-1891, 16(8), OSA, Washington, D.C. (11 pages).
Qian, R. et al., "Characterization of Long Working Distance Optical Coherence Tomography for Imaging of Pediatric Retinal Pathology," TVST, Oct. 2017, 1-12, 6(5), ARVO Journals, Rockville. (10 pages).
OCT Sub-Study Committee for the NORDIC Idiopathic Intracranial Hypertension Study Group, "Baseline OCT Measurements in the Idiopathic Intracranial Hypertension Treatment Trial, Part I: Quality Control, Comparisons, and Variability," Investigative Ophthalmology & Visual Science, Dec. 2014, 8180-8188, 55(12), ARVO Journals, Rockville. (9 pages).
Wojtkowski, M. et al., "In vivo human retinal imaging by Fourier domain optical coherence tomography," Journal of Biomedical Optics, Jul. 2002, 457-463, 7(3), SPIE, Bellingham. (7 pages).
PCT Search Report and Written Opinion for corresponding PCT International Application No. PCT/US20/15598 dated Apr. 16, 2020.

* cited by examiner

SYSTEMS AND METHODS FOR IMAGING A TARGET FEATURE OF A SUBJECT BASED ON TRACKED POSITIONS OF THE SUBJECT AND THE TARGET FEATURE

CROSS REFERENCE TO RELATED APPLICATIONS

This application is a 371 application of PCT International Patent Application No. PCT/US2020/015598 and filed on Jan. 29, 2020, which claims priority to U.S. Patent Application No. 62/798,052, filed Jan. 29, 2019, and titled ROBOTICALLY-ALIGNED OPTICAL COHERENCE TOMOGRAPHY FOR AUTOMATIC IMAGING OF STATIONARY AND MOVING EYES; the contents of which are incorporated herein by reference in their entireties.

FEDERALLY SPONSORED RESEARCH OR DEVELOPMENT

This invention was made with government support under Federal Grant Nos. F30-EY027280, R01-EY029302, and U01-EY028079, awarded by the National Institutes of Health (NIH). The government has certain rights to this invention.

TECHNICAL FIELD

The presently disclosed subject matter relates generally to imaging systems. Particularly, the presently disclosed subject matter relates to systems and methods for imaging a target feature of a subject based on the tracked positions of the subject and the target feature.

BACKGROUND

Optical coherence tomography (OCT) has revolutionized structural imaging in the eye's anterior segment and retina. Ophthalmologists now routinely employ OCT in managing ocular diseases, including age-related macular degeneration, diabetic retinopathy, glaucoma, and corneal edema. Unfortunately, clinical OCT systems designed for such purposes are commonly large tabletop instruments sequestered in dedicated imaging suites of ophthalmology offices or large eye centers. Moreover, they require mechanical head stabilization (e.g., chinrests or forehead straps) for eye alignment and motion suppression, as well as trained ophthalmic photographers for operation. OCT imaging is consequently restricted to non-urgent evaluations of cooperative patients in ophthalmology care settings due to modern systems' poor portability, stabilization needs, and operator skill requirements. Rather than an ubiquitous tool available in both routine and emergent care environments, OCT is instead an exclusive imaging modality of the ocular specialist, restricted by imaging workspace and operator barriers.

Efforts are underway to lower these barriers, albeit individually. From an operator skill standpoint, manufacturers of several commercial OCT systems have incorporated self-alignment into their tabletop scanners. While easy to operate, such systems still depend on chinrests for approximate alignment and motion stabilization. Furthermore, the optical and mechanical components necessary to achieve self-alignment add significant bulk and weight into an already large scanner. From an imaging workspace standpoint, handheld OCT shrinks and lightens the scanner such that the operator can articulate it with ease. The OCT scanner is brought to the patient, as opposed to tabletop systems which do the reverse. Scans obtained in this manner become limited by manual alignment and motion artifacts, such that only highly skilled operators with steady hands reliably succeed. Image registration techniques effectively mitigate small motion artifacts in post-processing; however, these algorithms are fundamentally limited by the raw image quality. In those cases where the raw image is lost due to misalignment, no correction is possible. Neither self-aligning tabletop nor handheld scanners overcome the workspace and operator skill barriers that restrict routine OCT imaging to cooperative, ambulatory patients. Self-aligning tabletop scanners still require mechanical head stabilization, and handheld scanners still require trained operators. Moreover, these two approaches are incompatible: the extra bulk of automated alignment components renders handheld scanners even more unwieldy.

In view of the foregoing, there is a need for improved systems and techniques for acquiring eye images, including image of the eye's anterior segment and retina. Particularly, there is a need for systems and techniques can permit an image scanner to be easily interface with the patient without operator training. Further, there is a need provide OCT imaging to acutely ill patients who physically cannot sit upright due to injury, strict bedrest, or loss of consciousness.

BRIEF DESCRIPTION OF THE DRAWINGS

Figure 1:
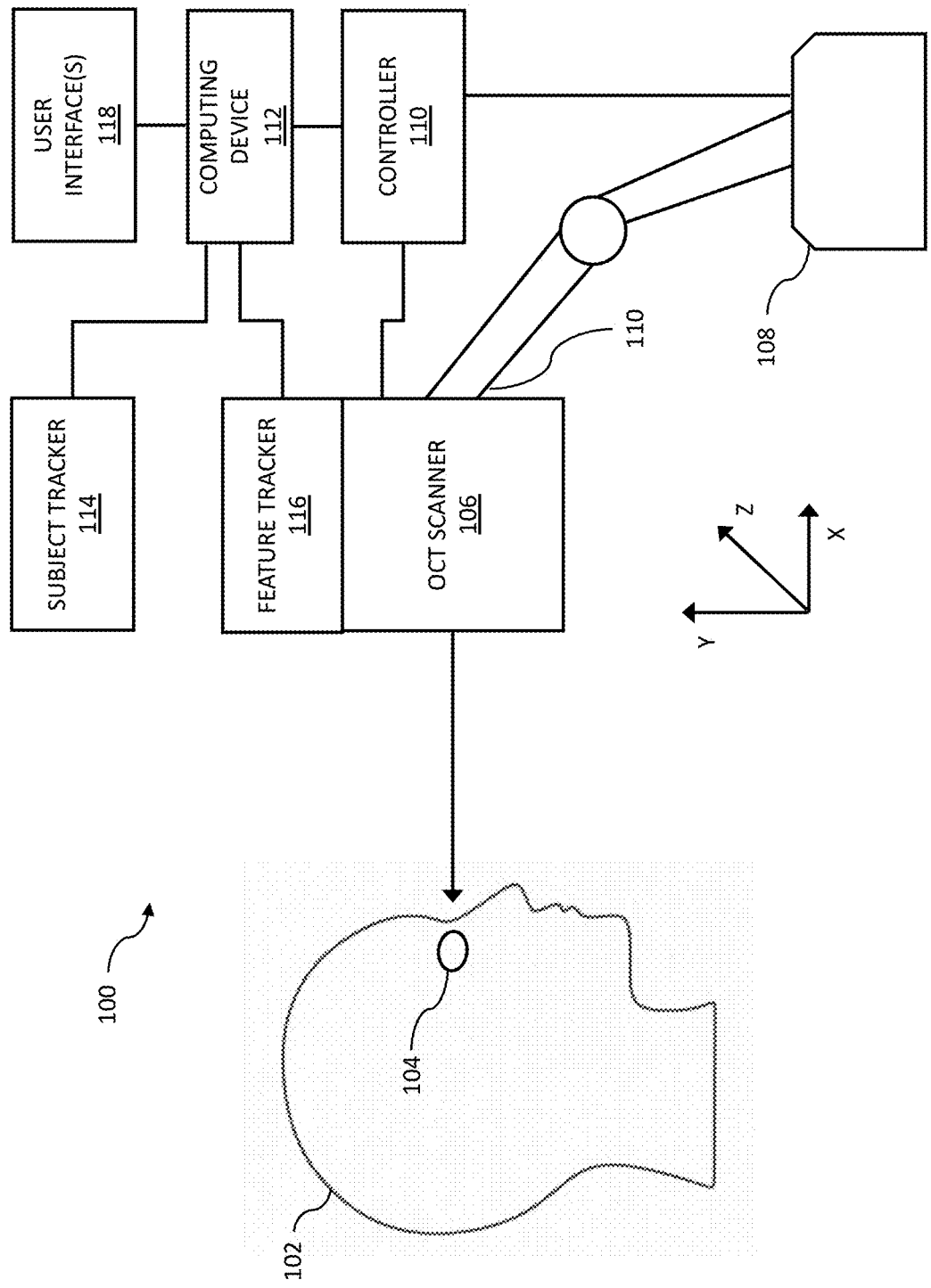
Figure 2:
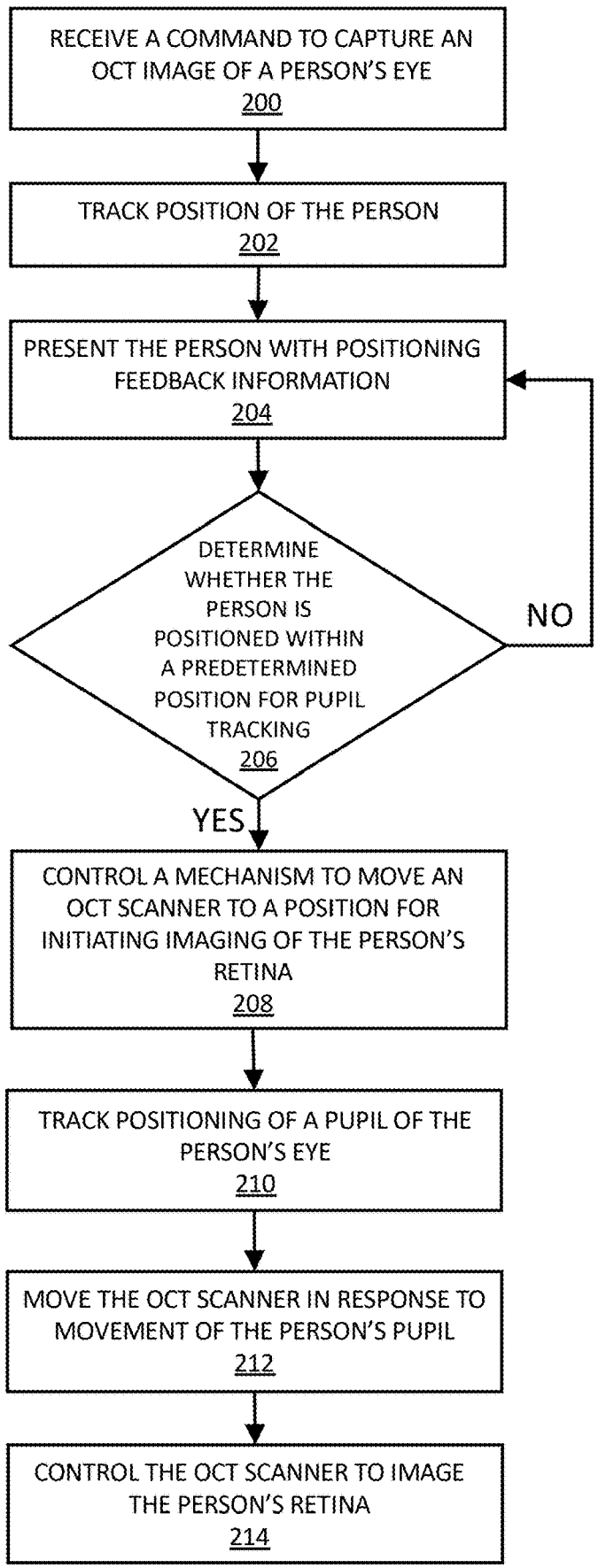
Figure 3:
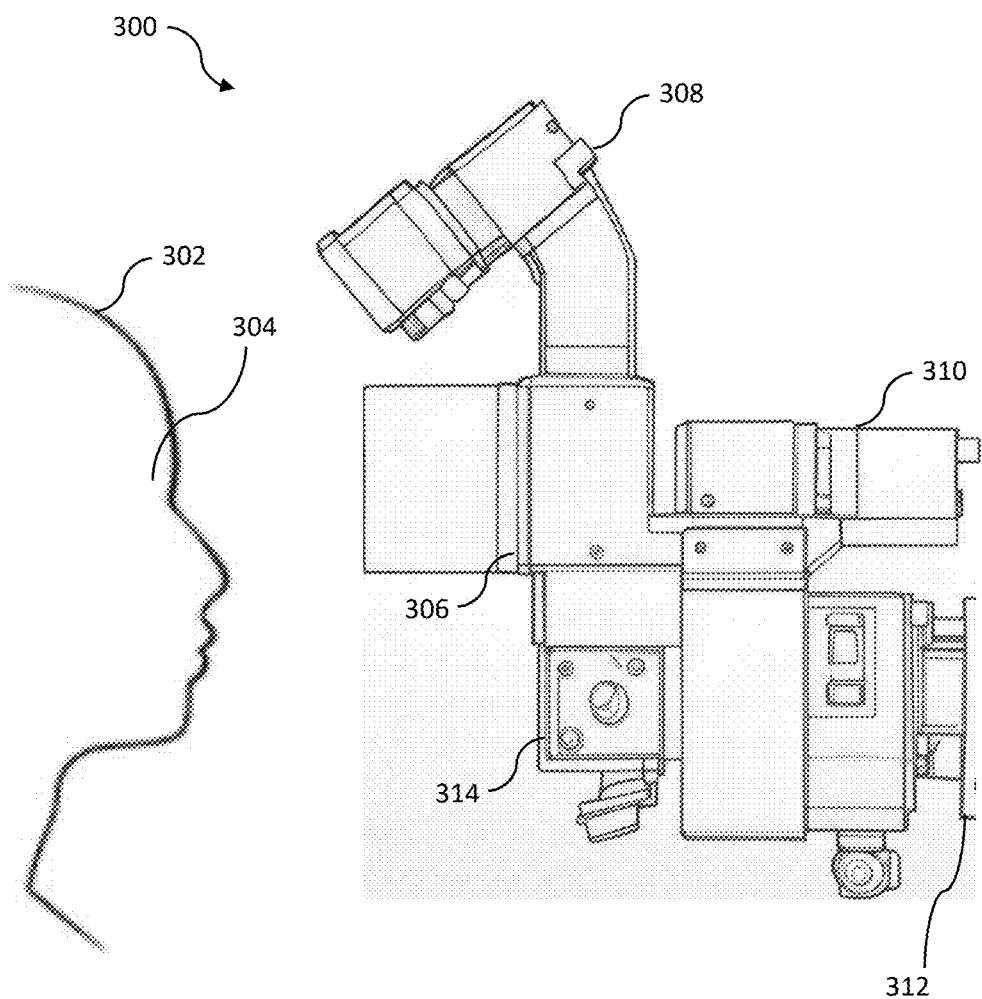
Figure 4:
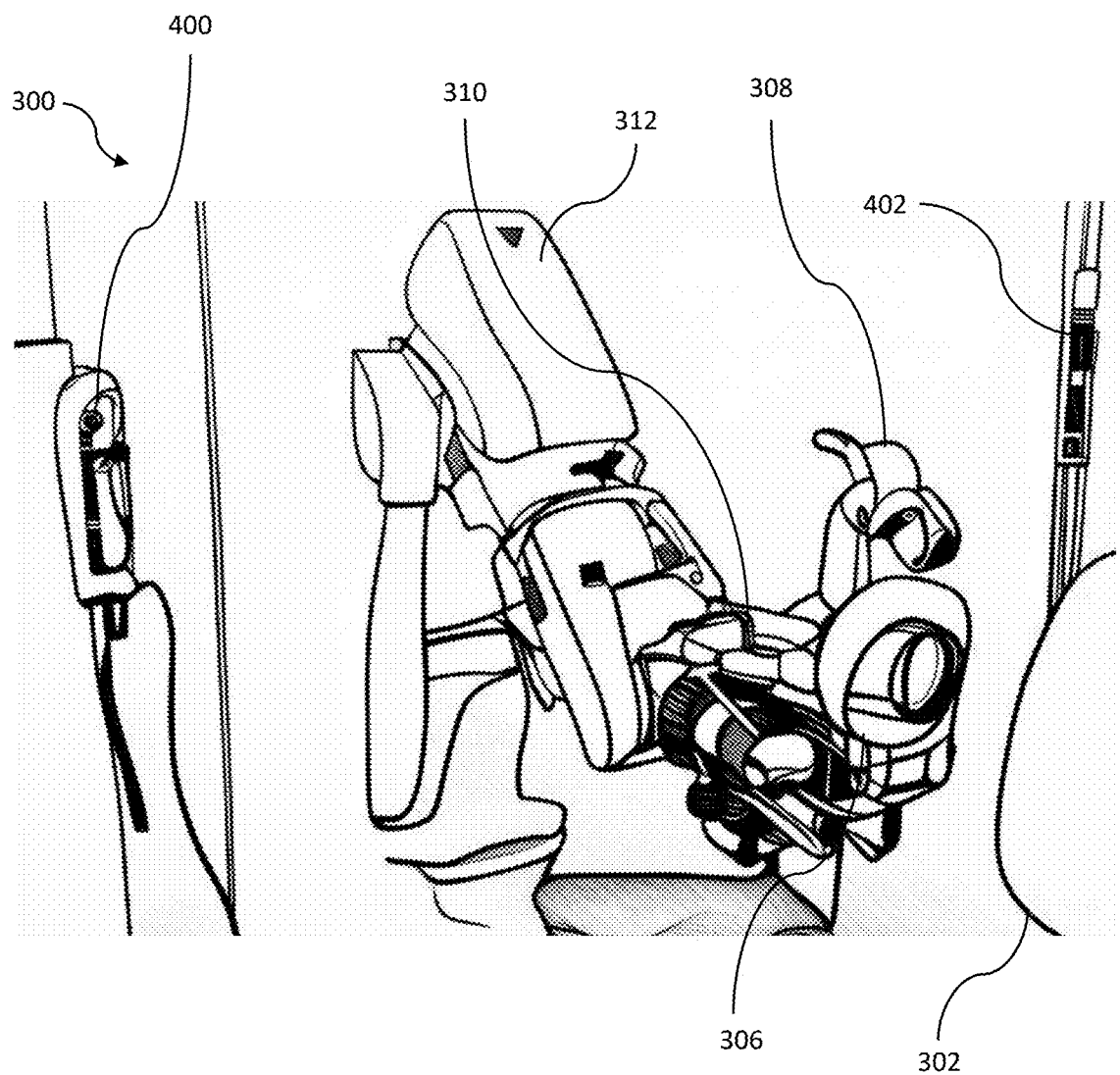
Figure 5C:
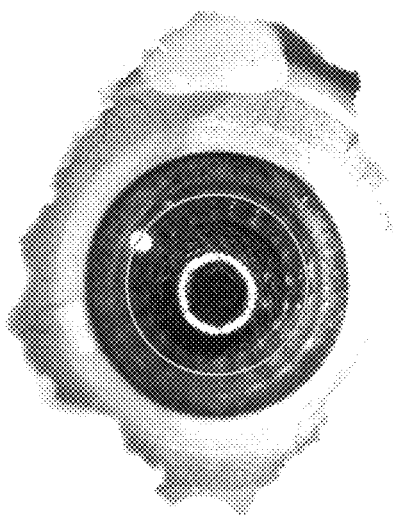
Figure 5B:
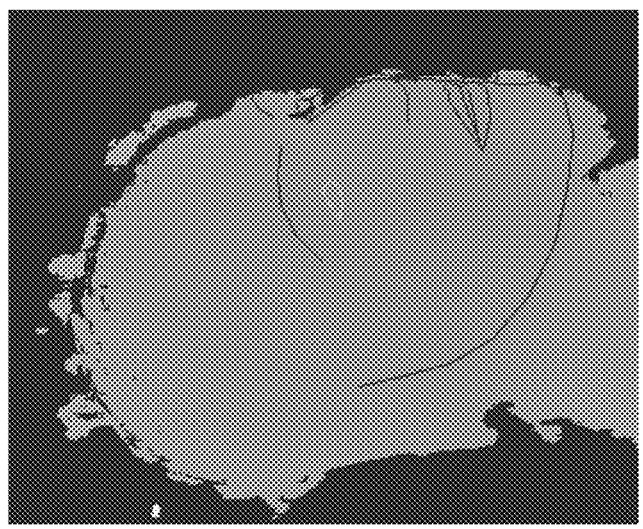
Figure 5A:
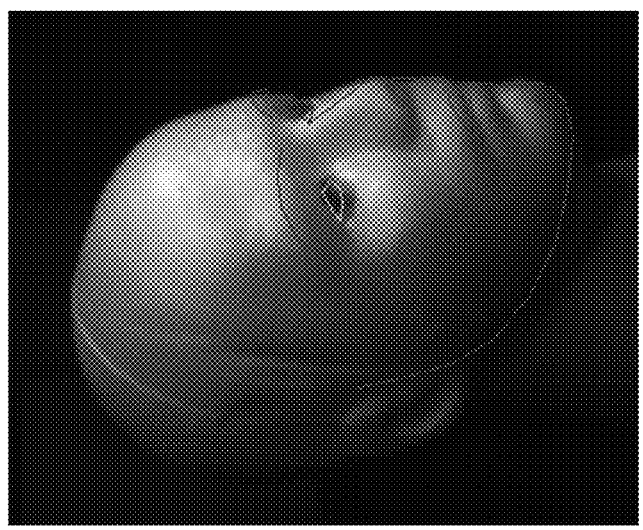
Figure 6:
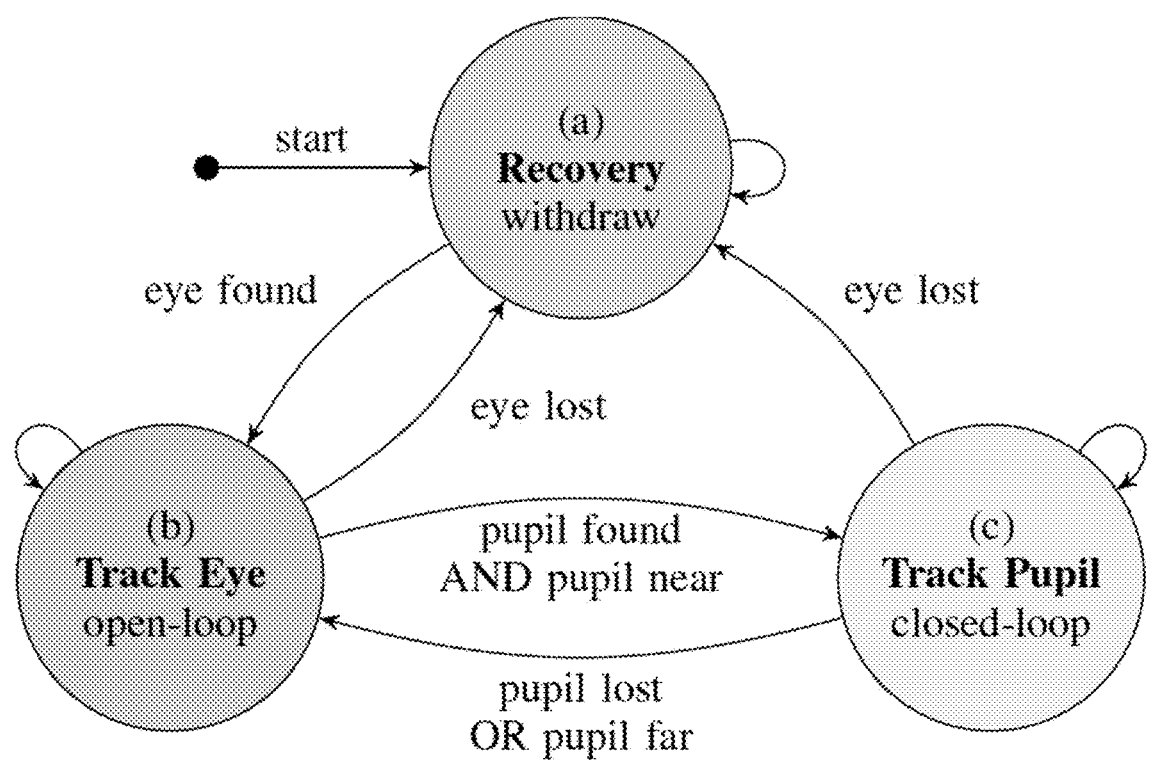
Figure 7:
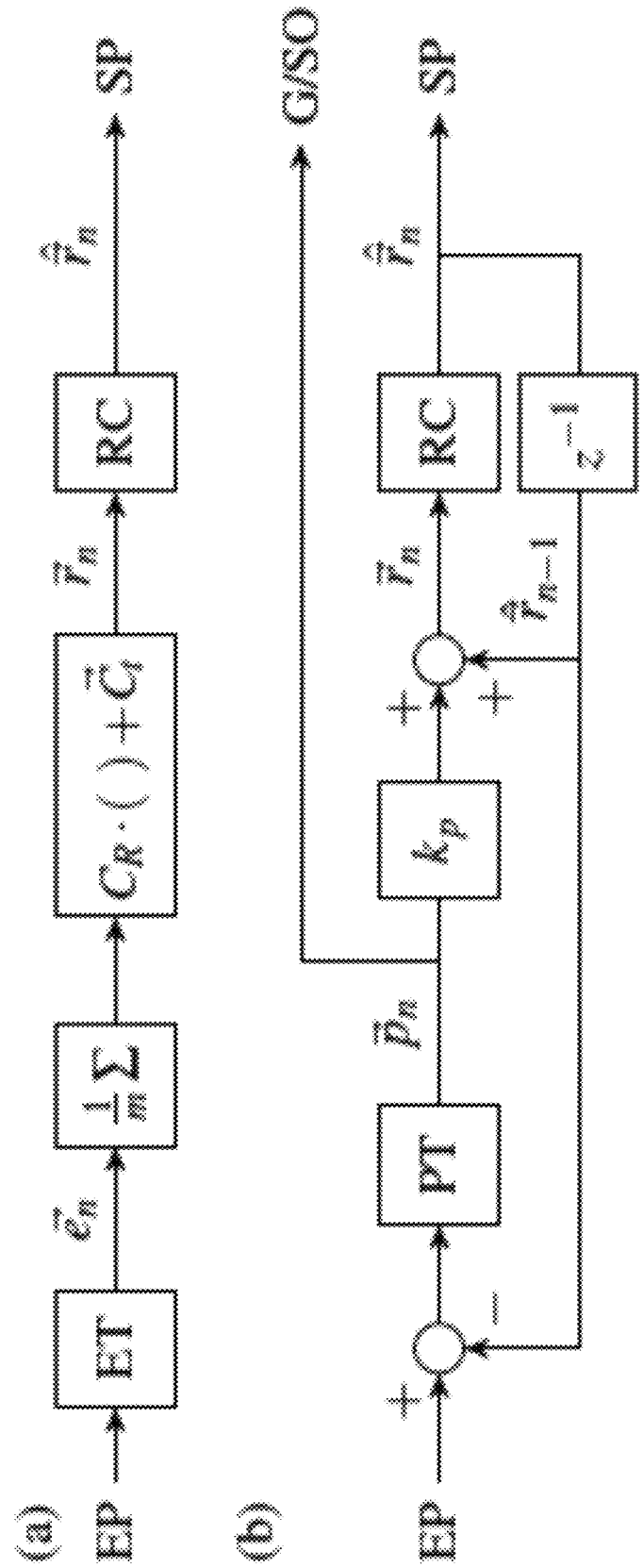
Figure 8:
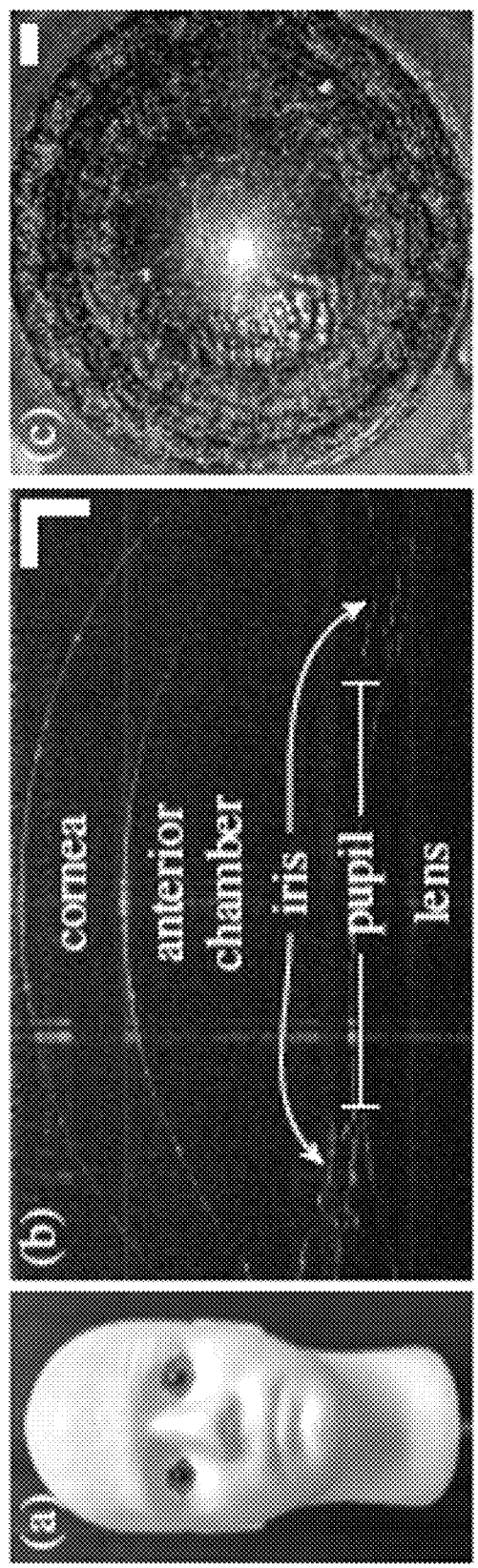
Figure 9:
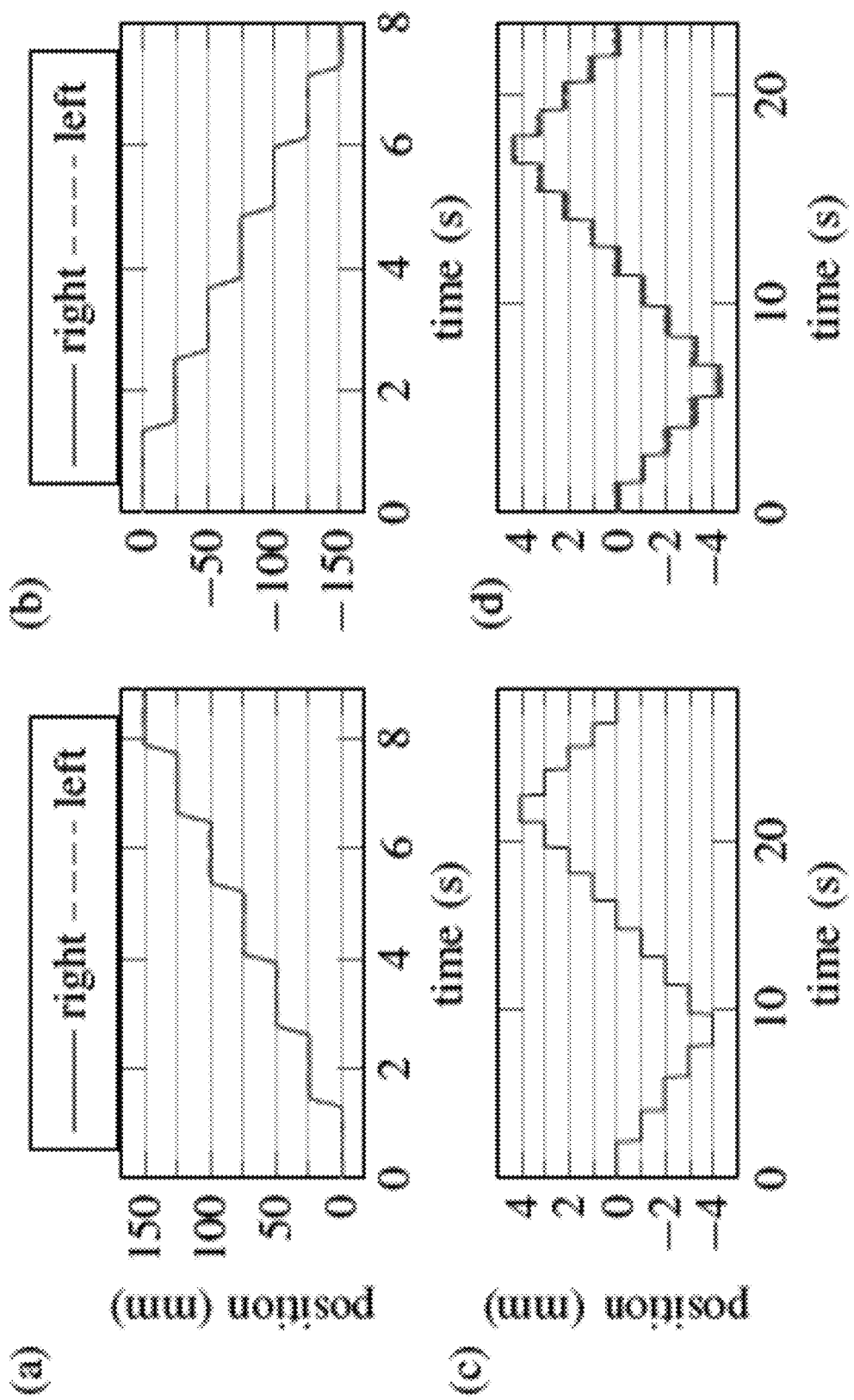
Figure 10:
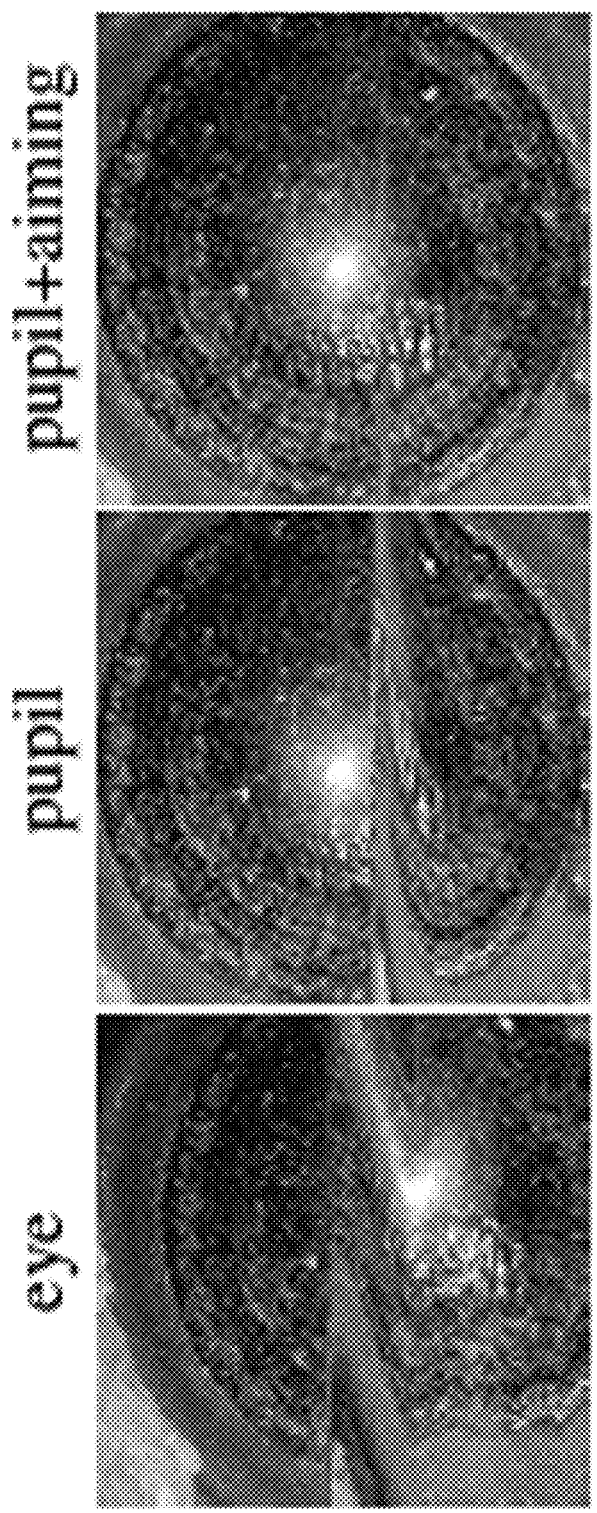
Figure 11:
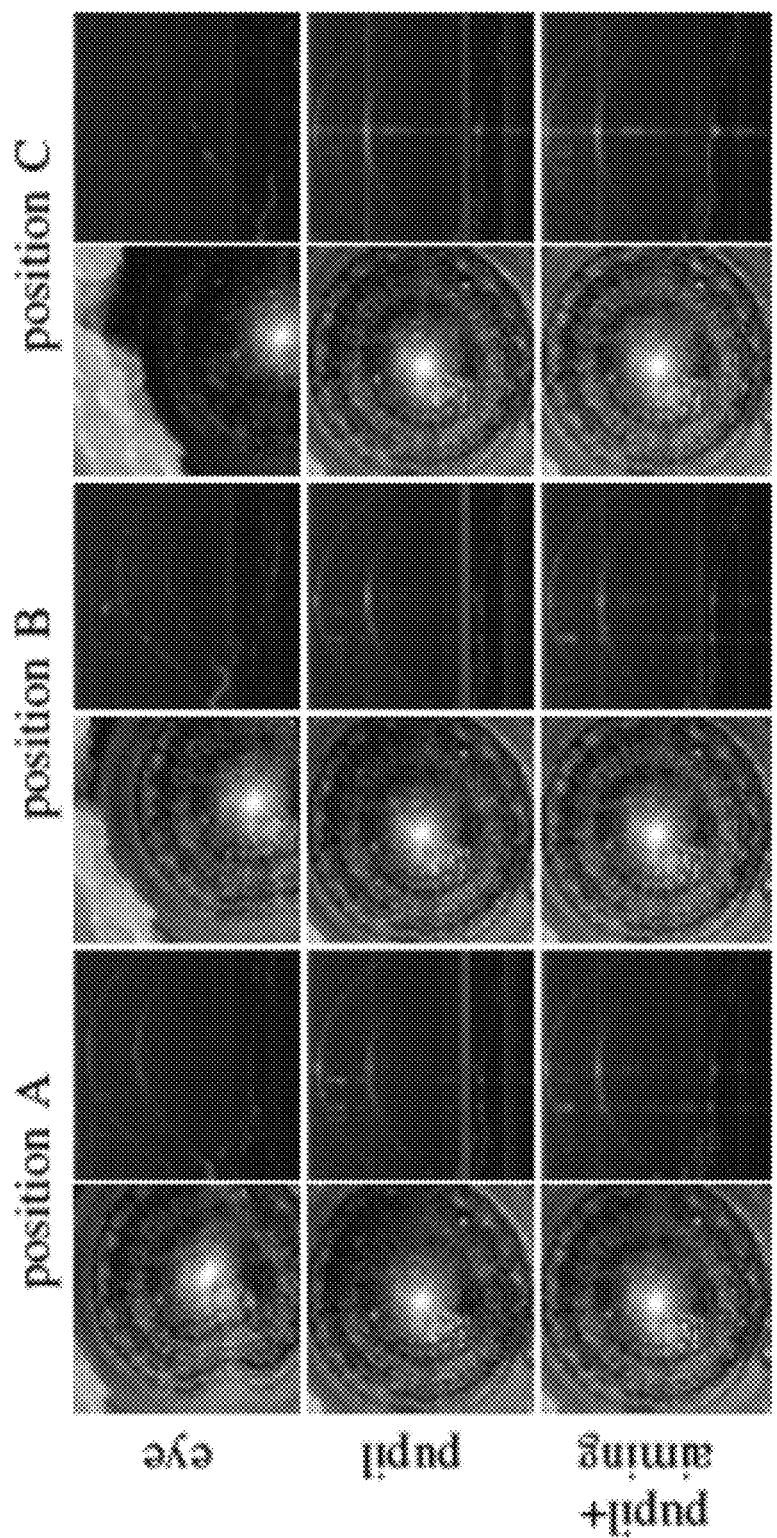
Figure 12:
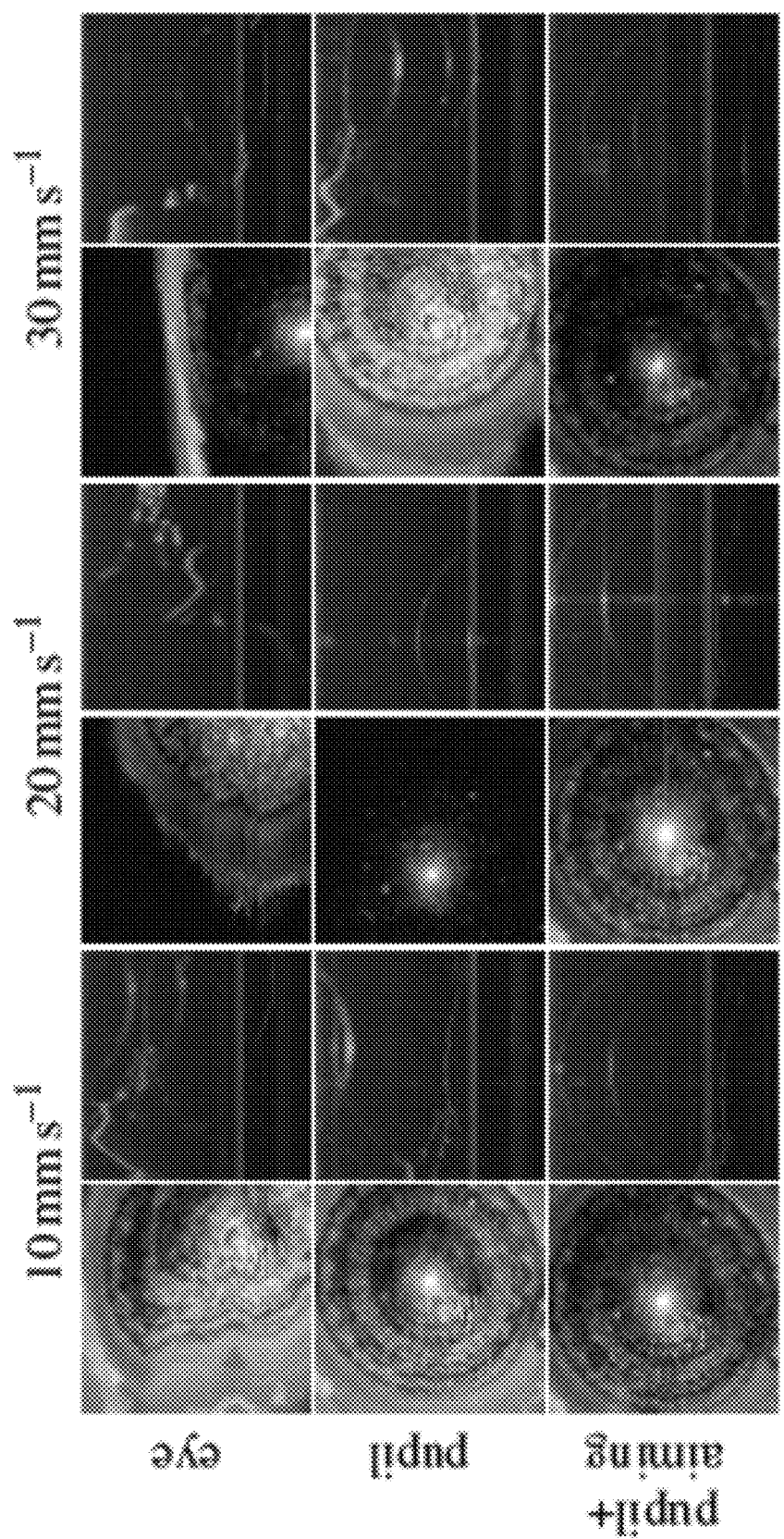
Figure 13:
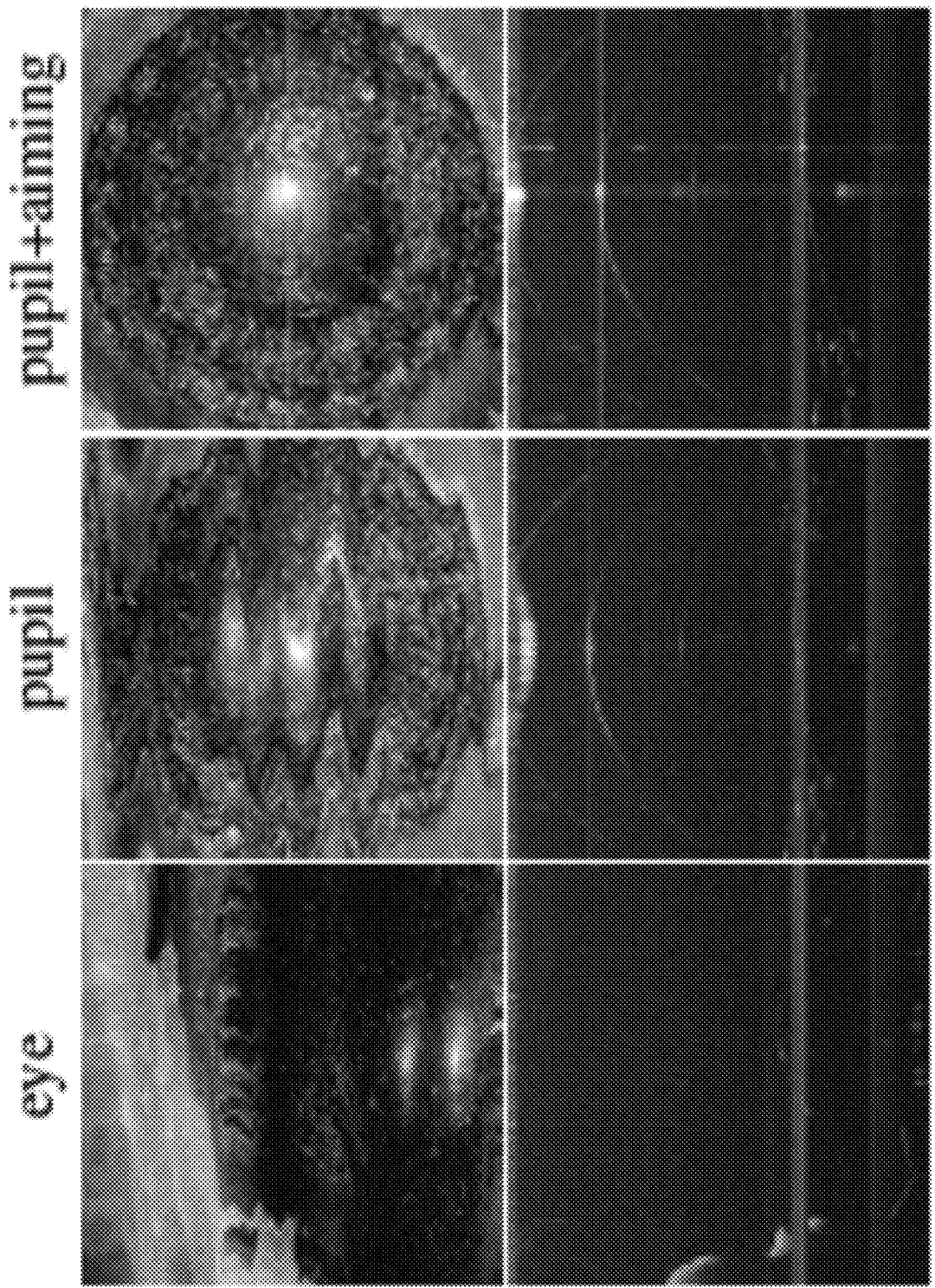
Figure 14:
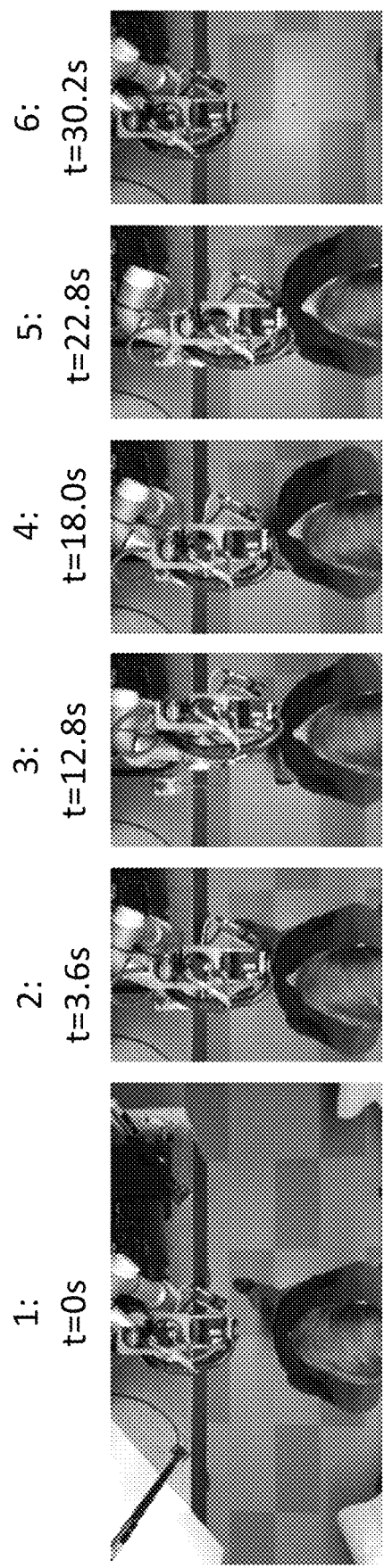
Figures 15, 16:
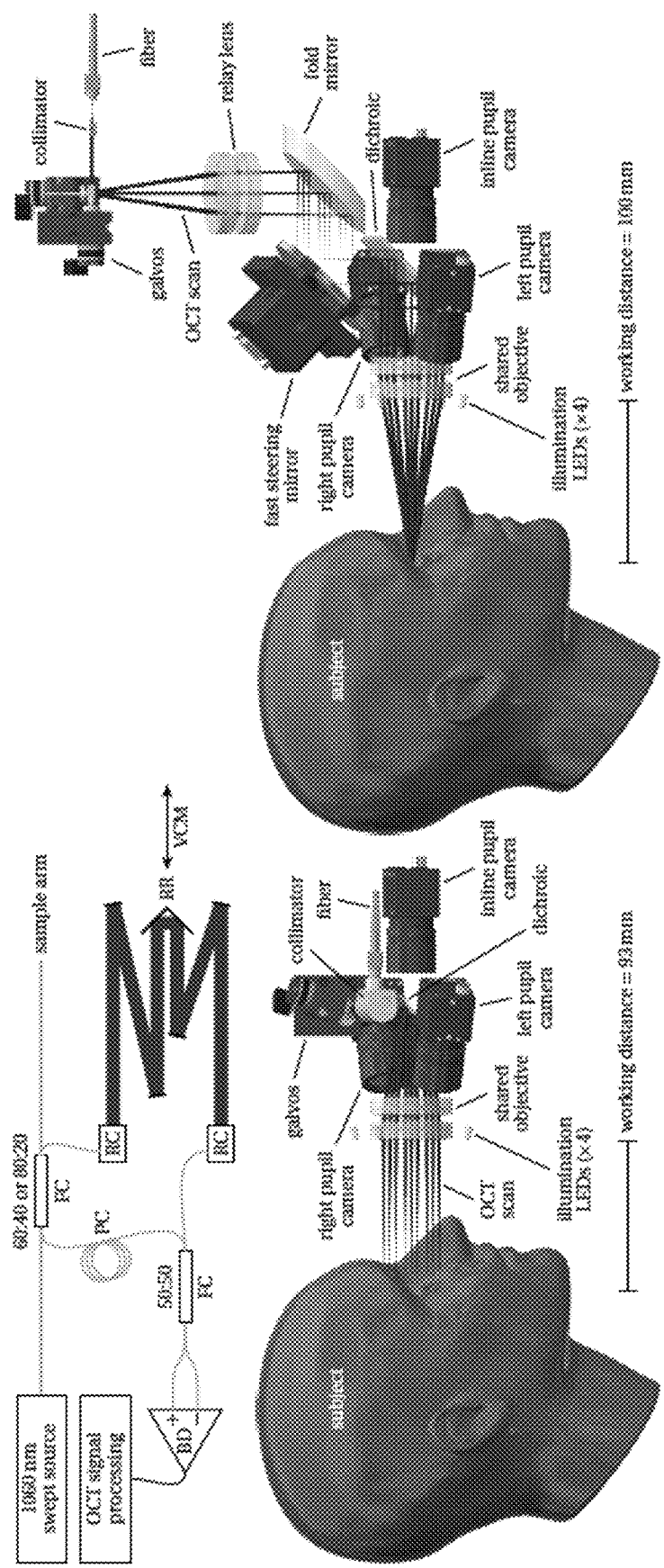
Figure 17:
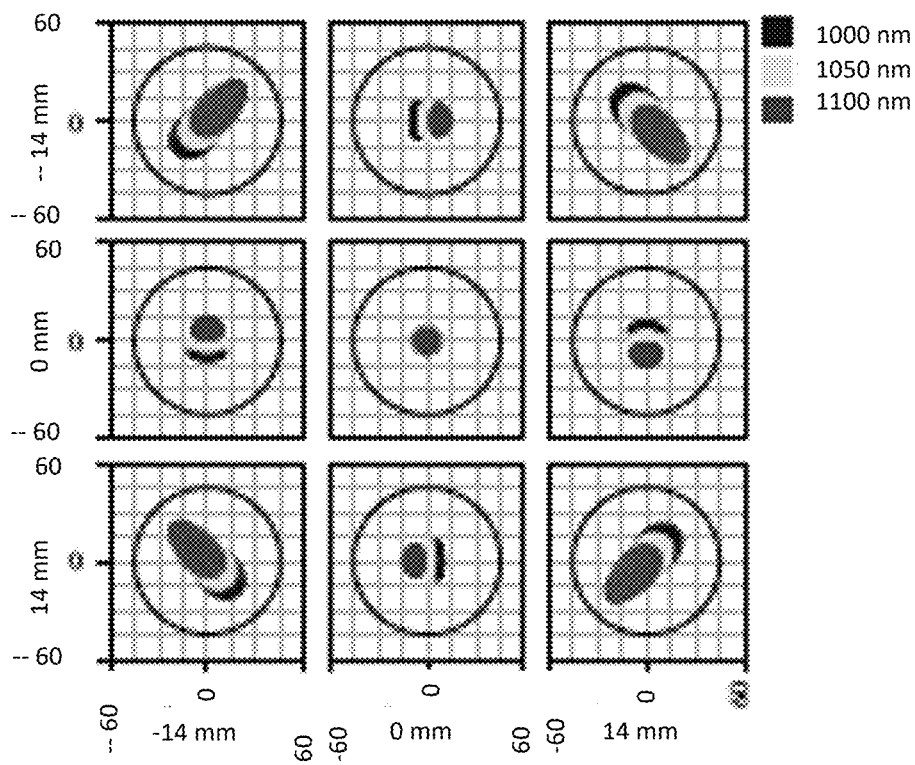
Figure 18:
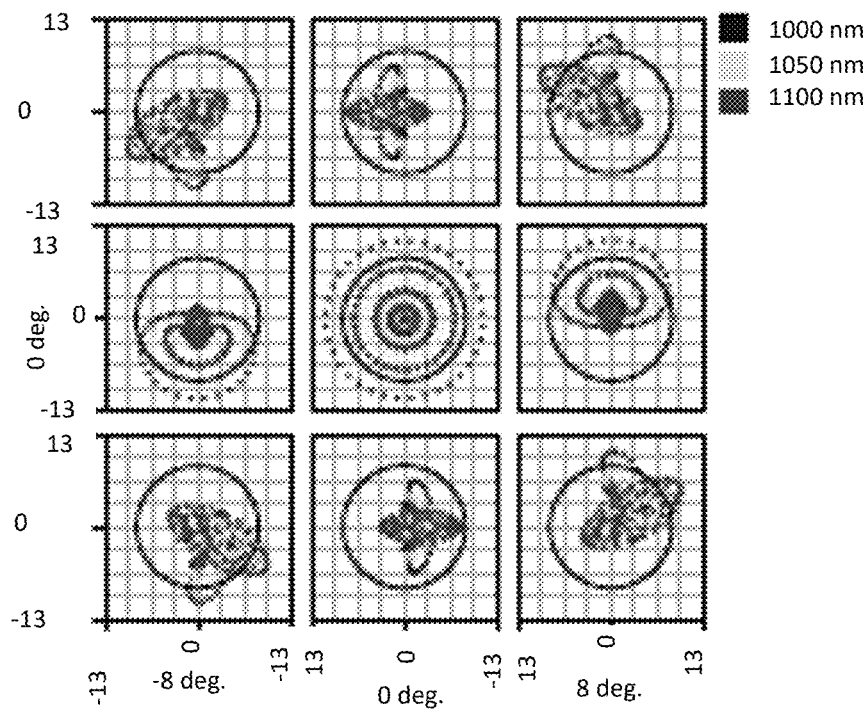
Figure 19:
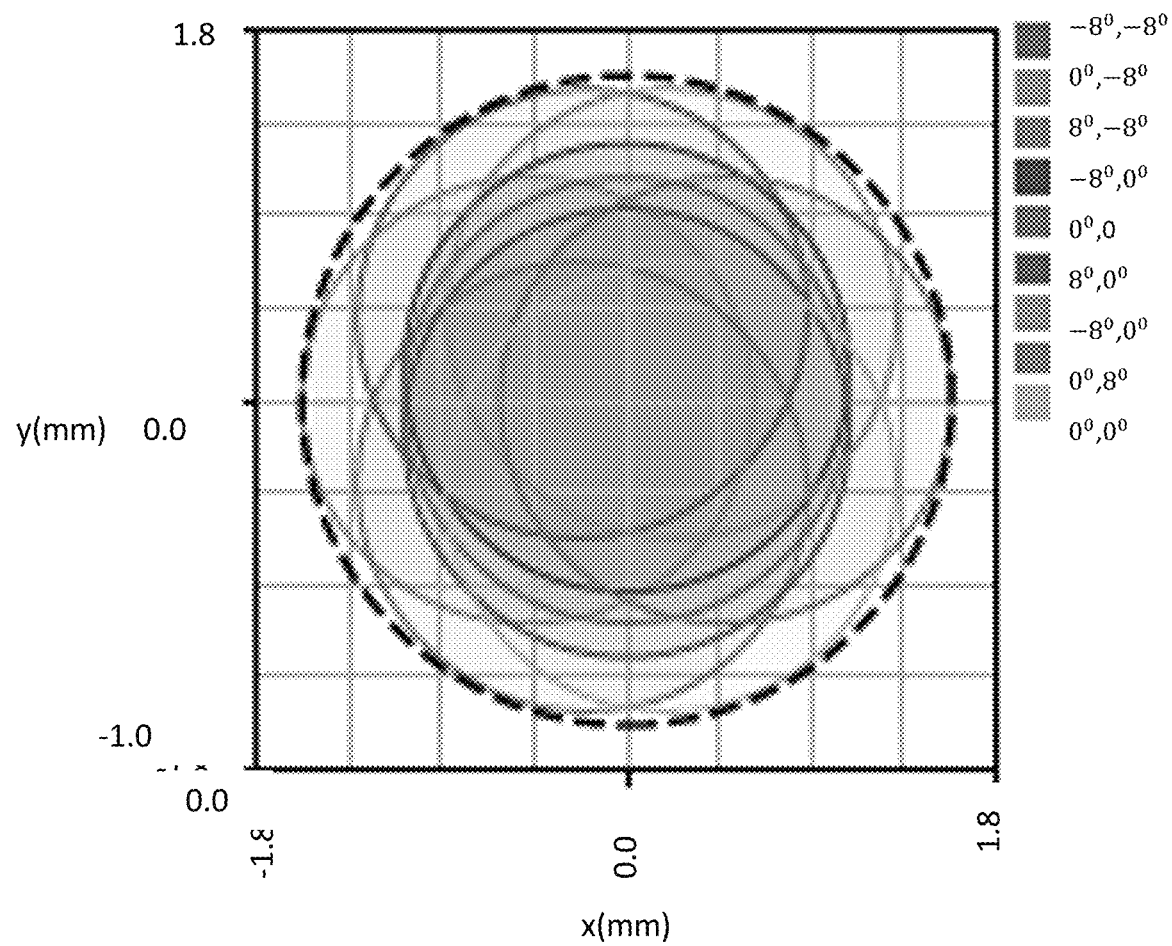
Figure 20:
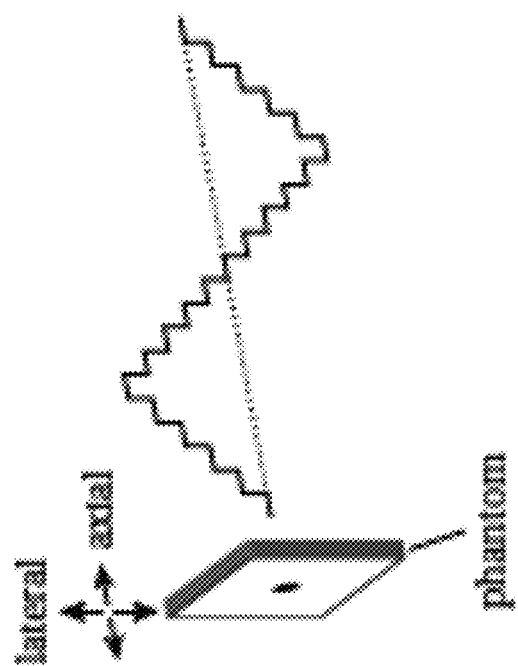
Figure 20:
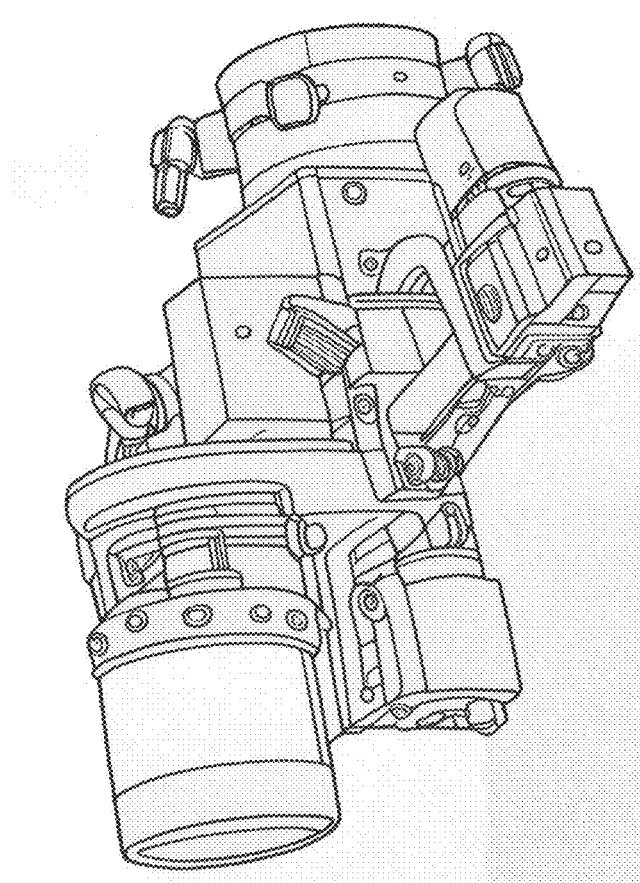
Figure 21:
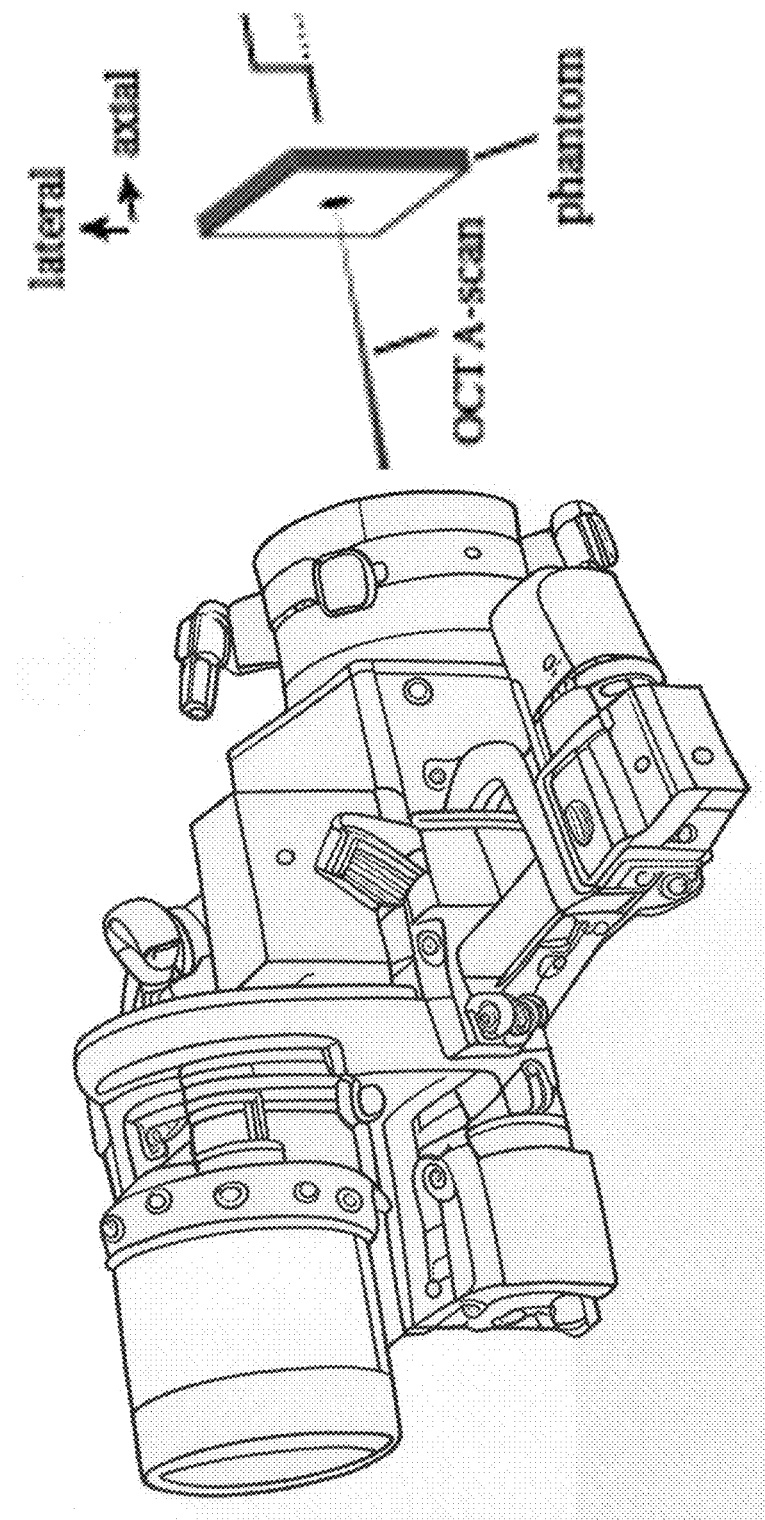
Figure 22:
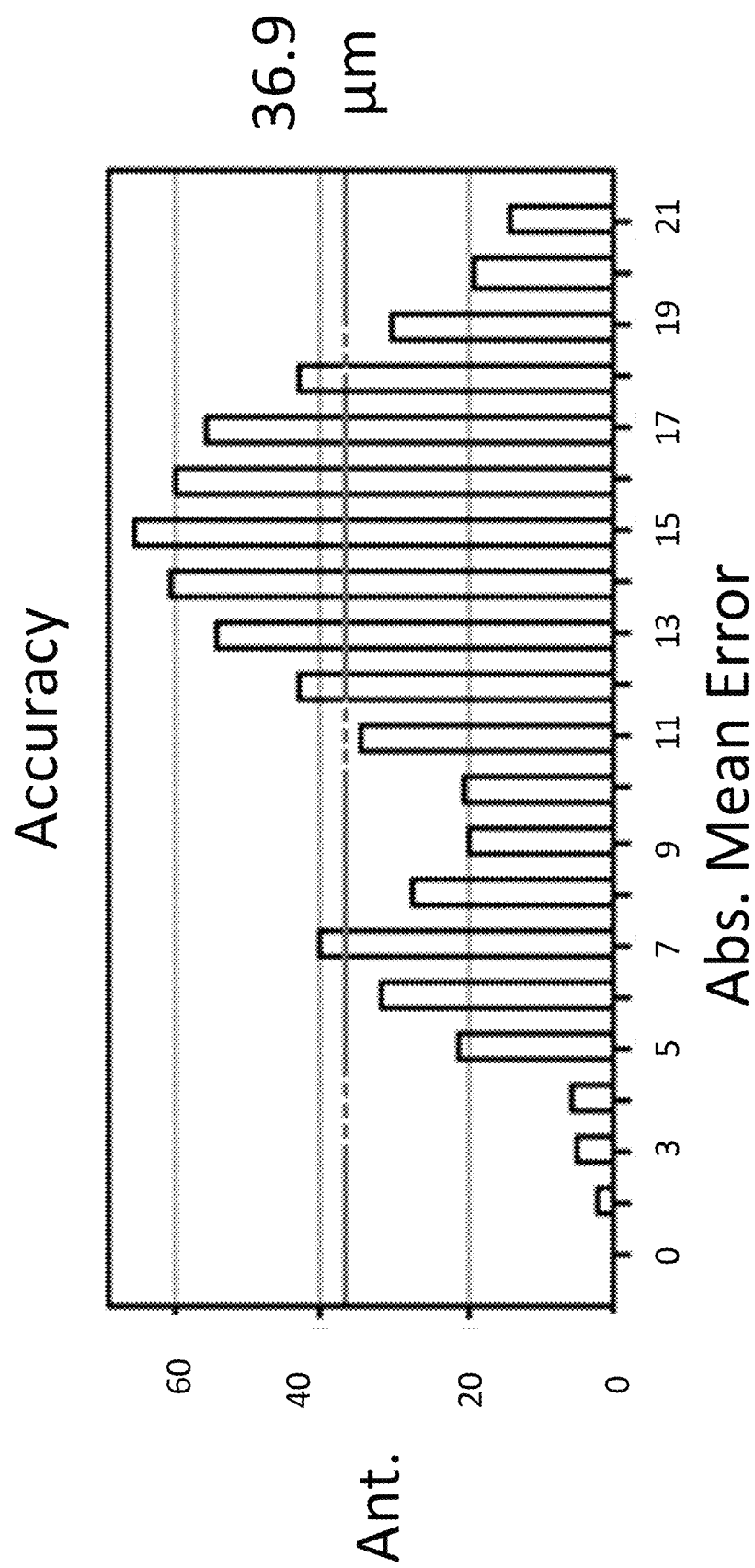
Figure 23:
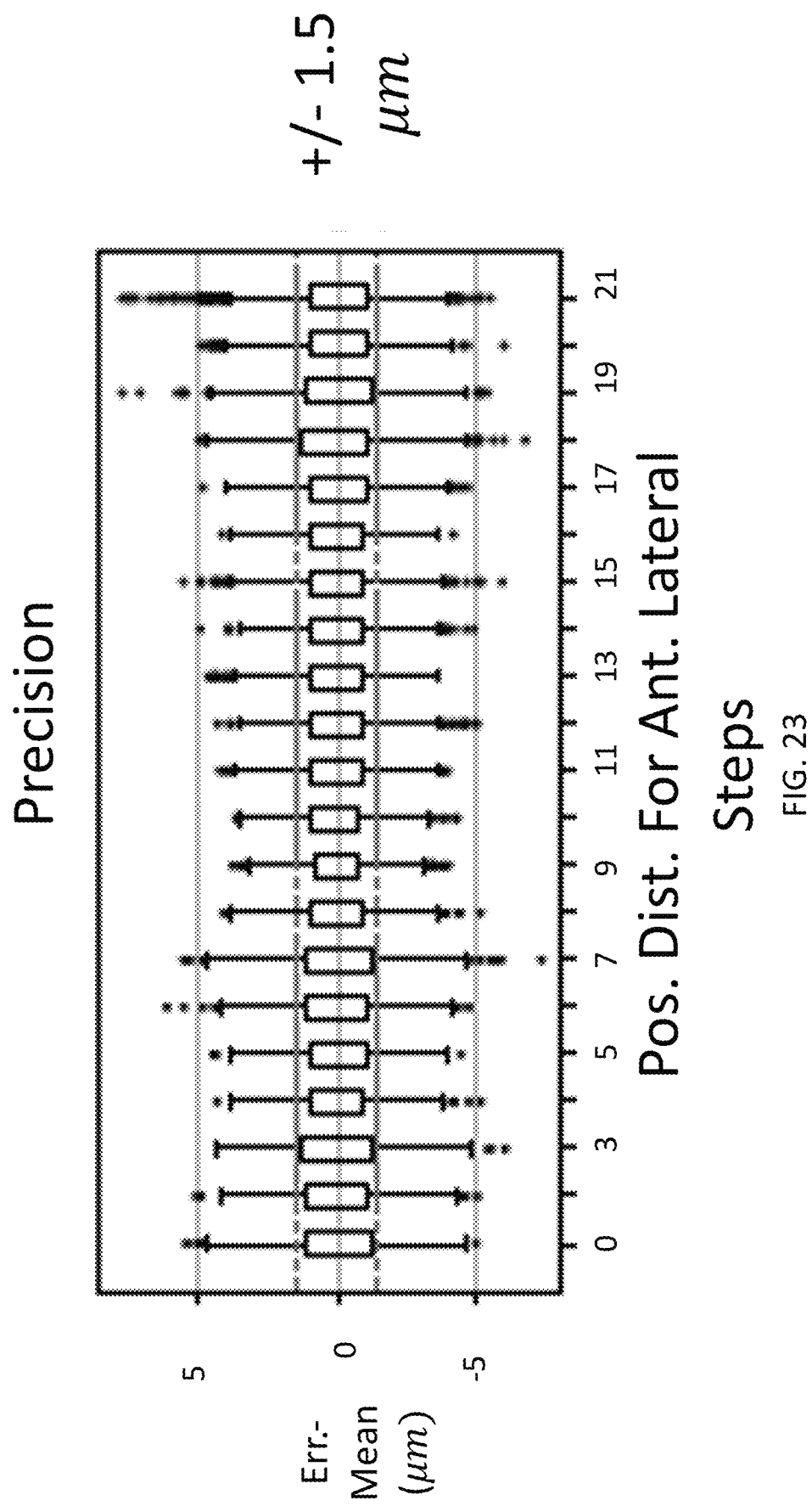
Figure 24:
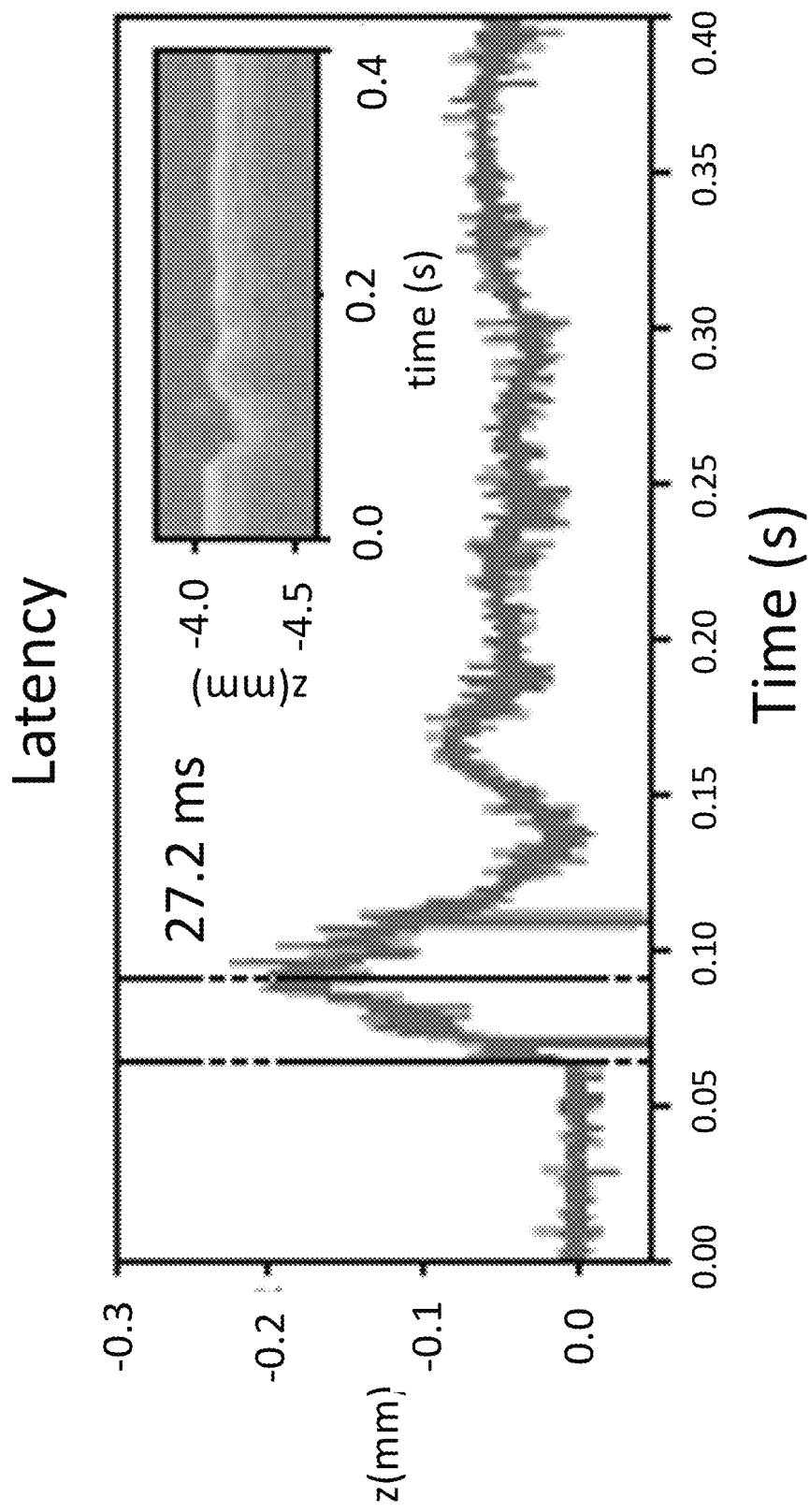
Figure 25:
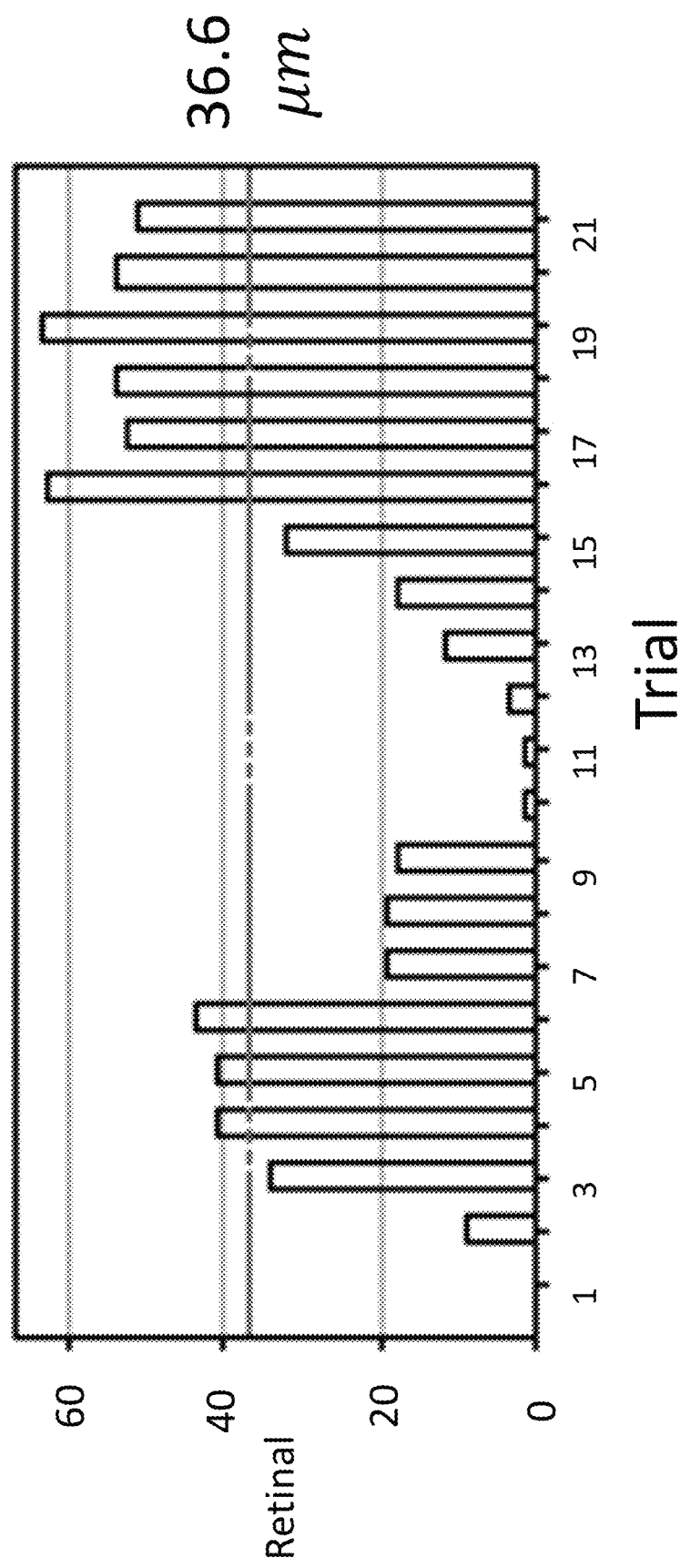
Figure 26:
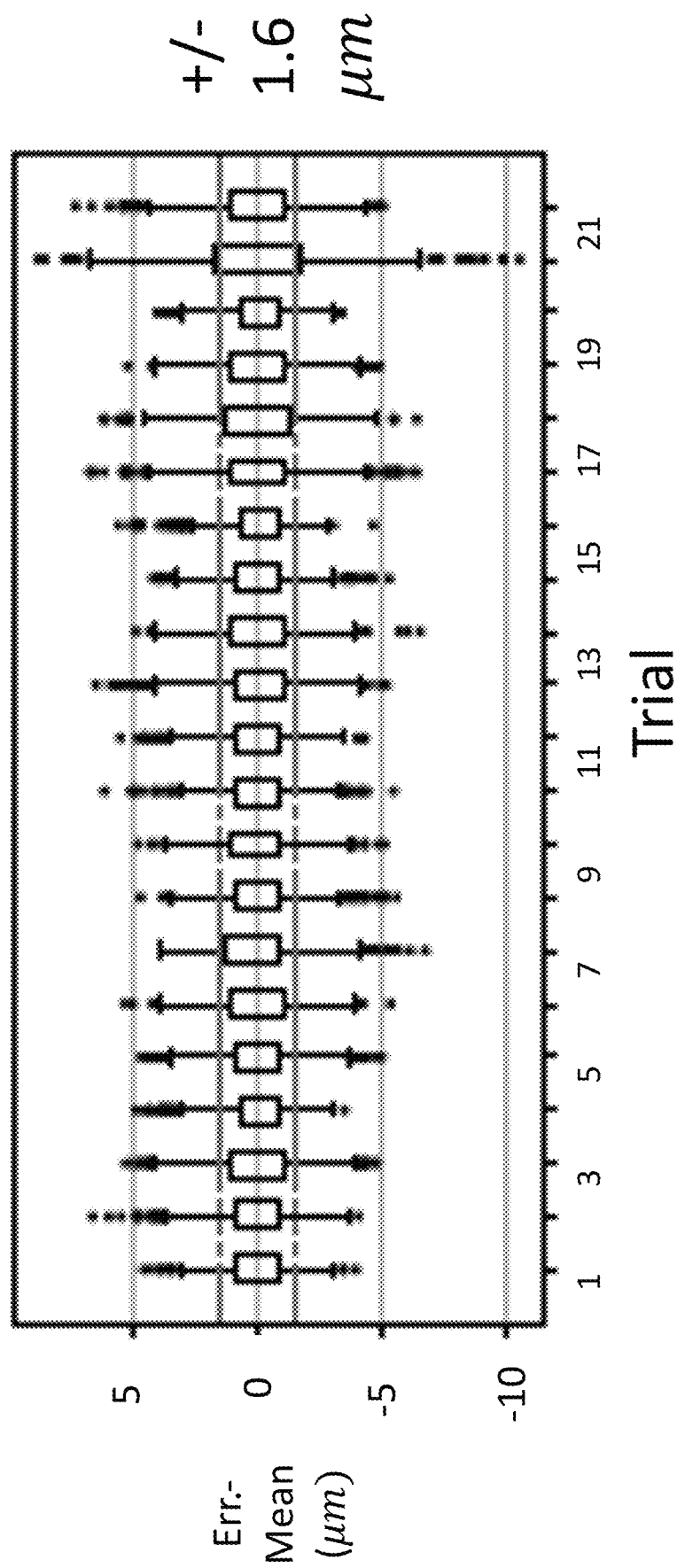
Figure 27:
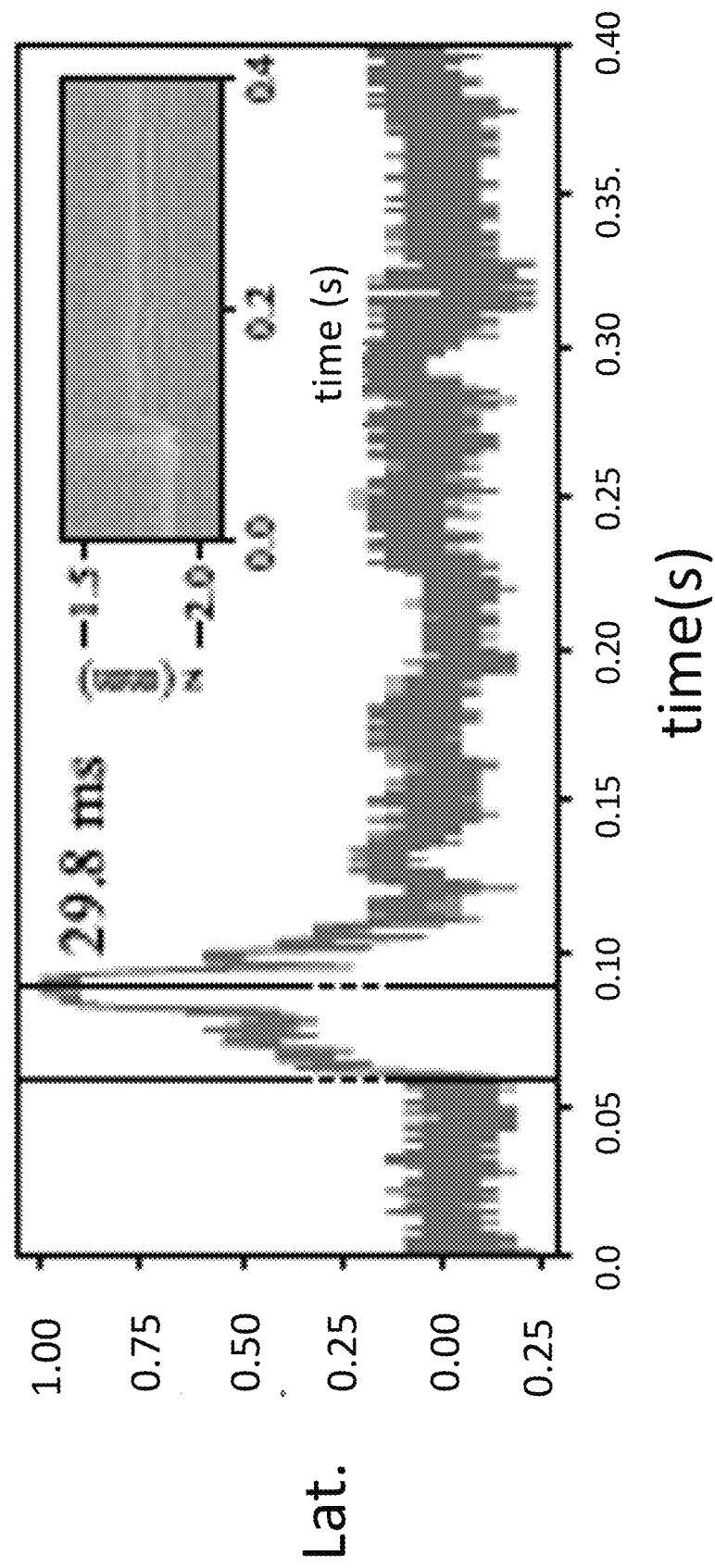
Figure 28:
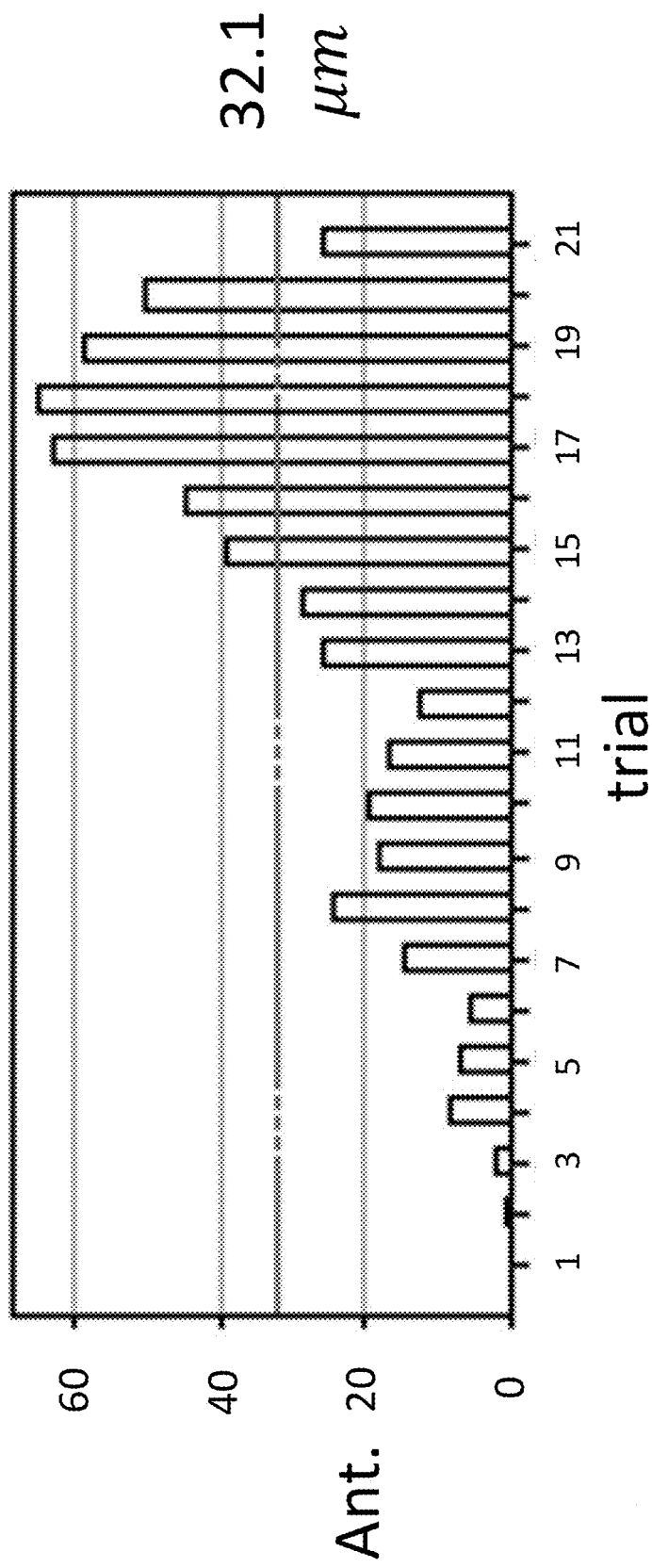
Figure 29:
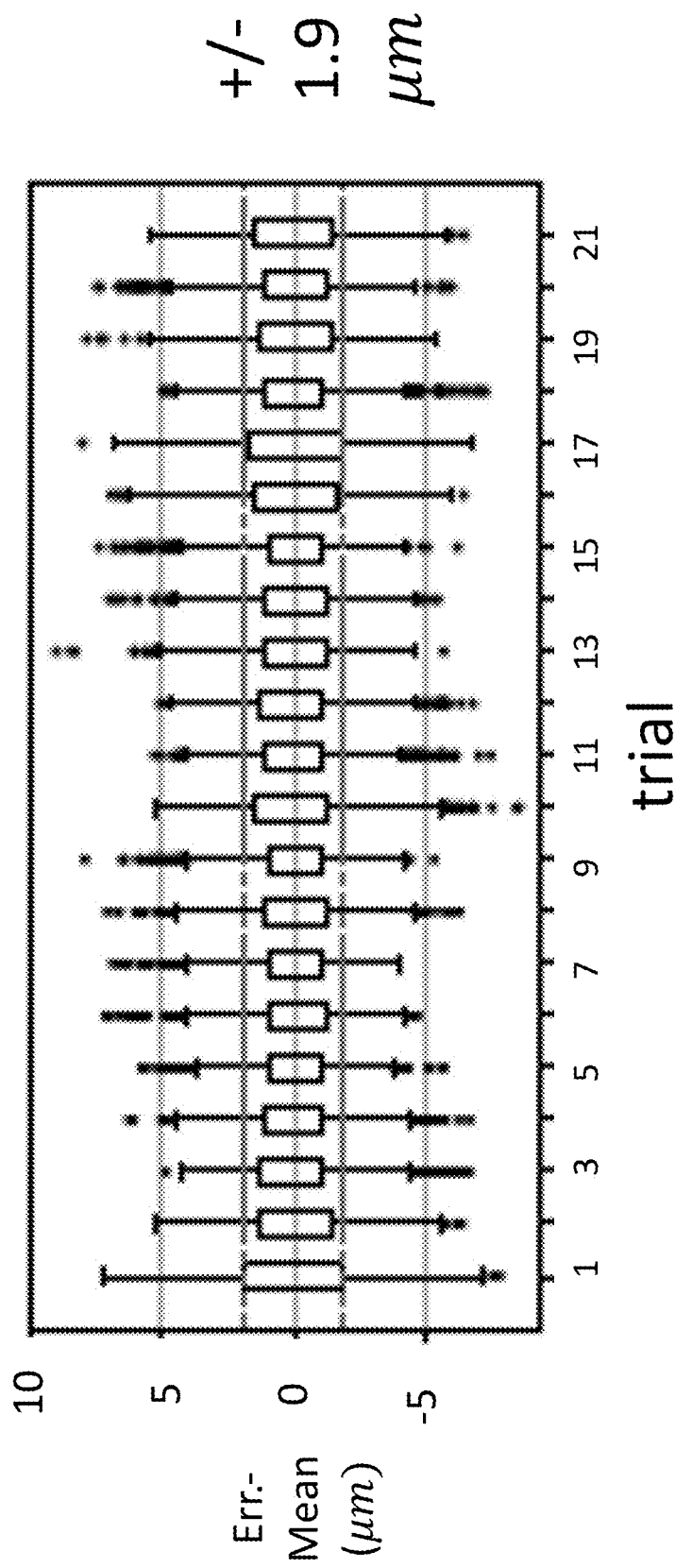
Figure 30:
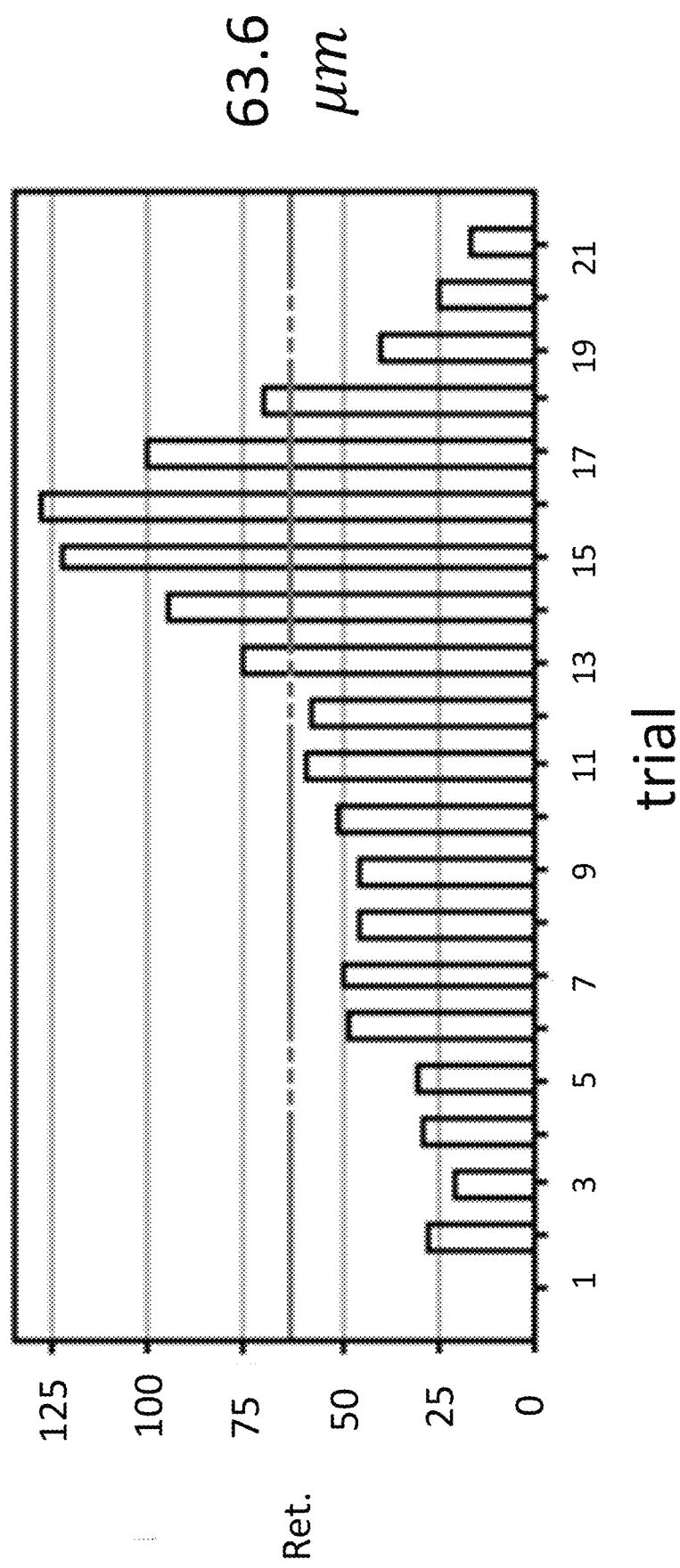
Figure 31:
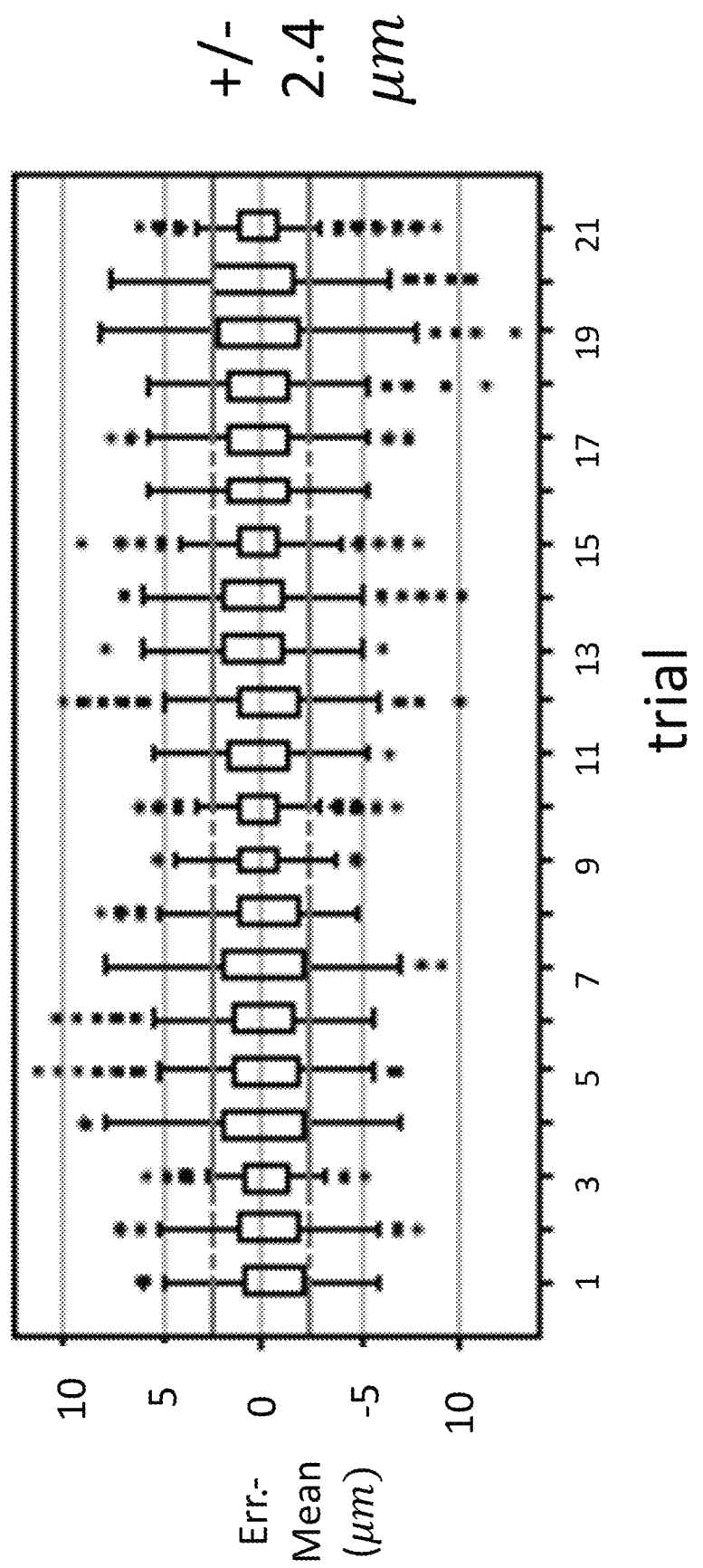
Figure 32:
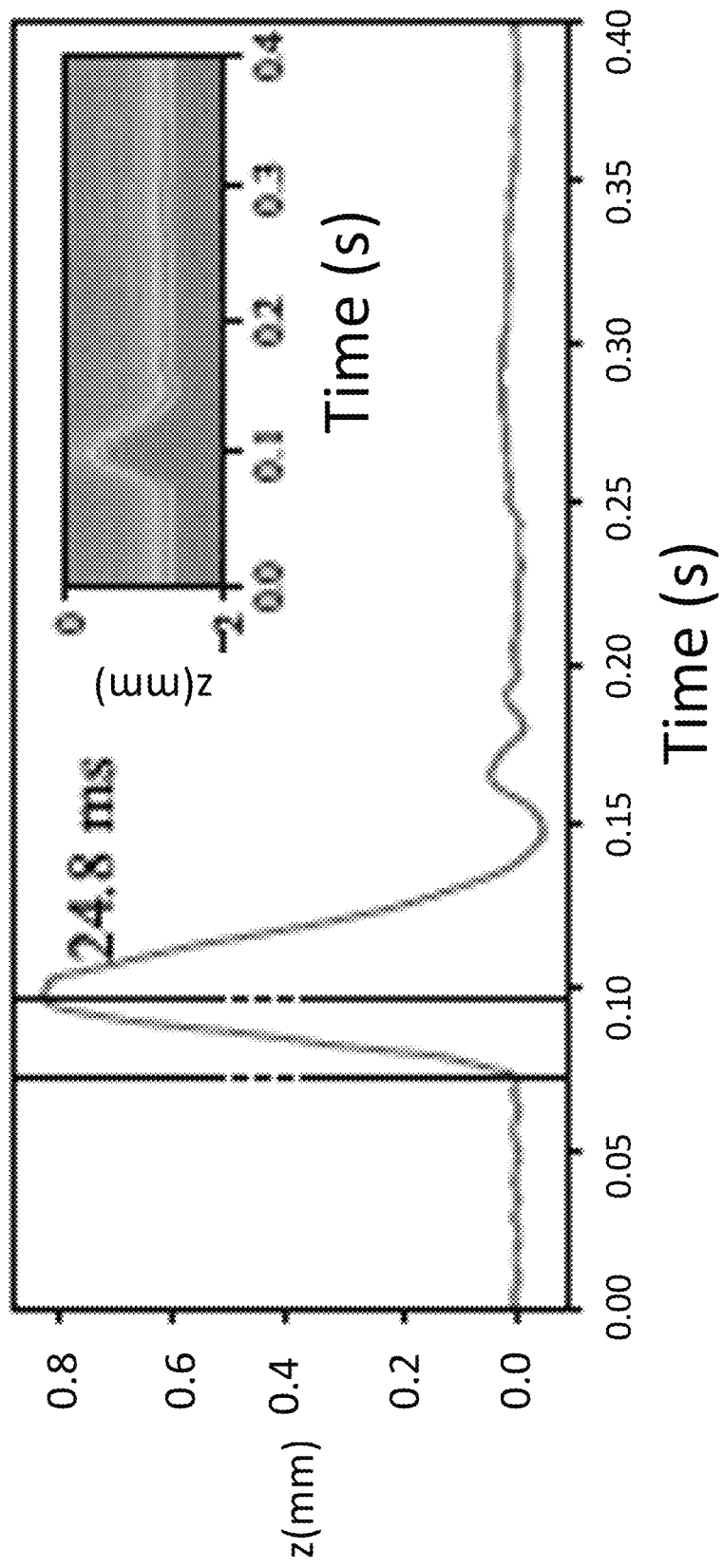
Figure 33:
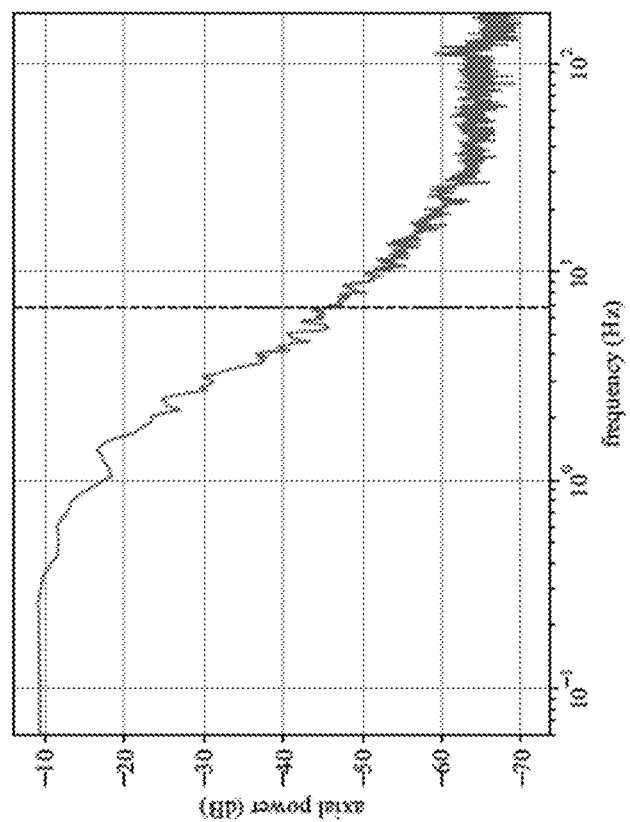
Figure 33:
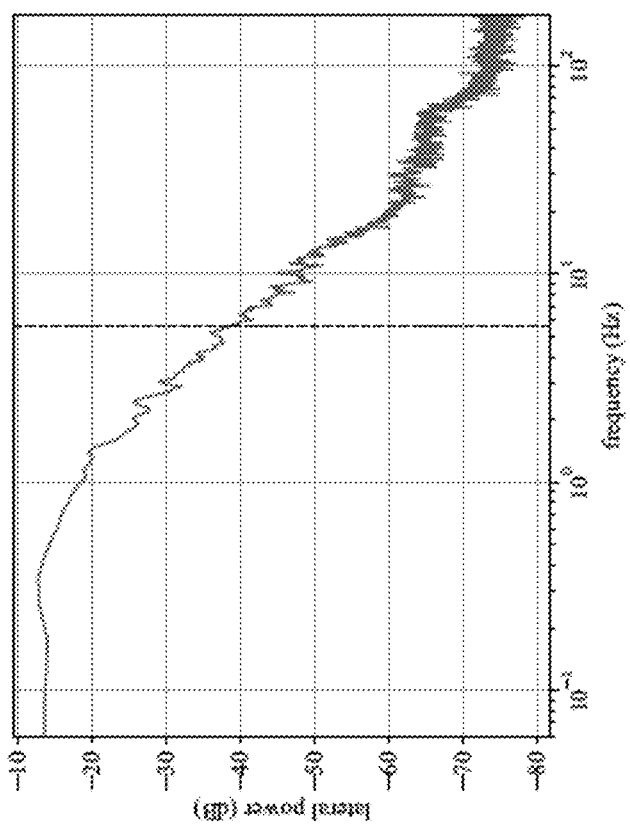
Figure 34A:
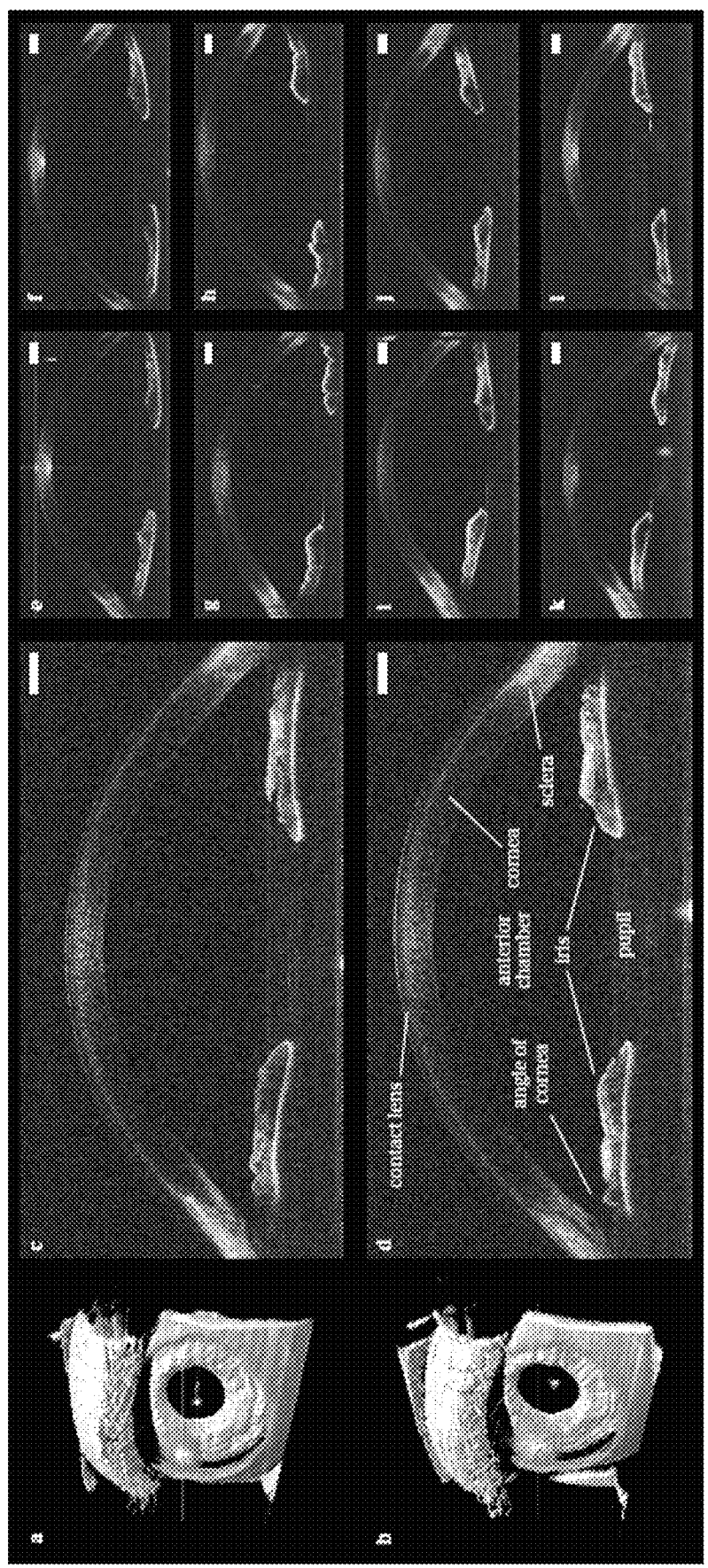
Figure 34B:
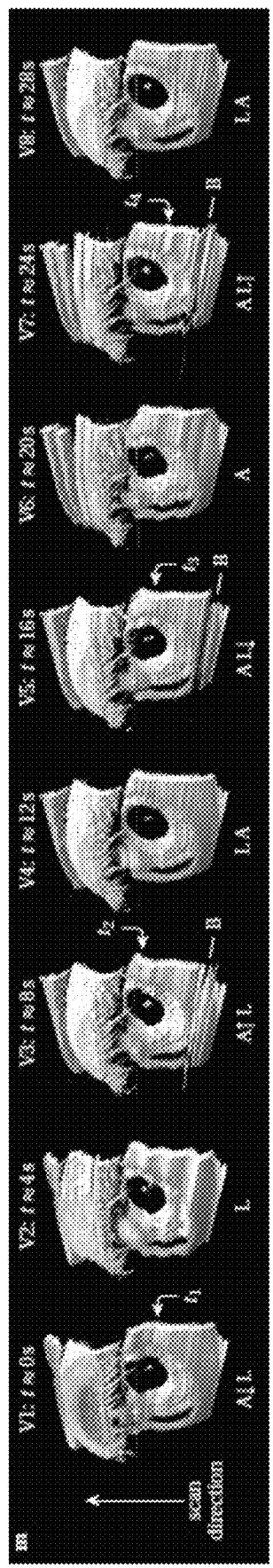
Figure 34C:
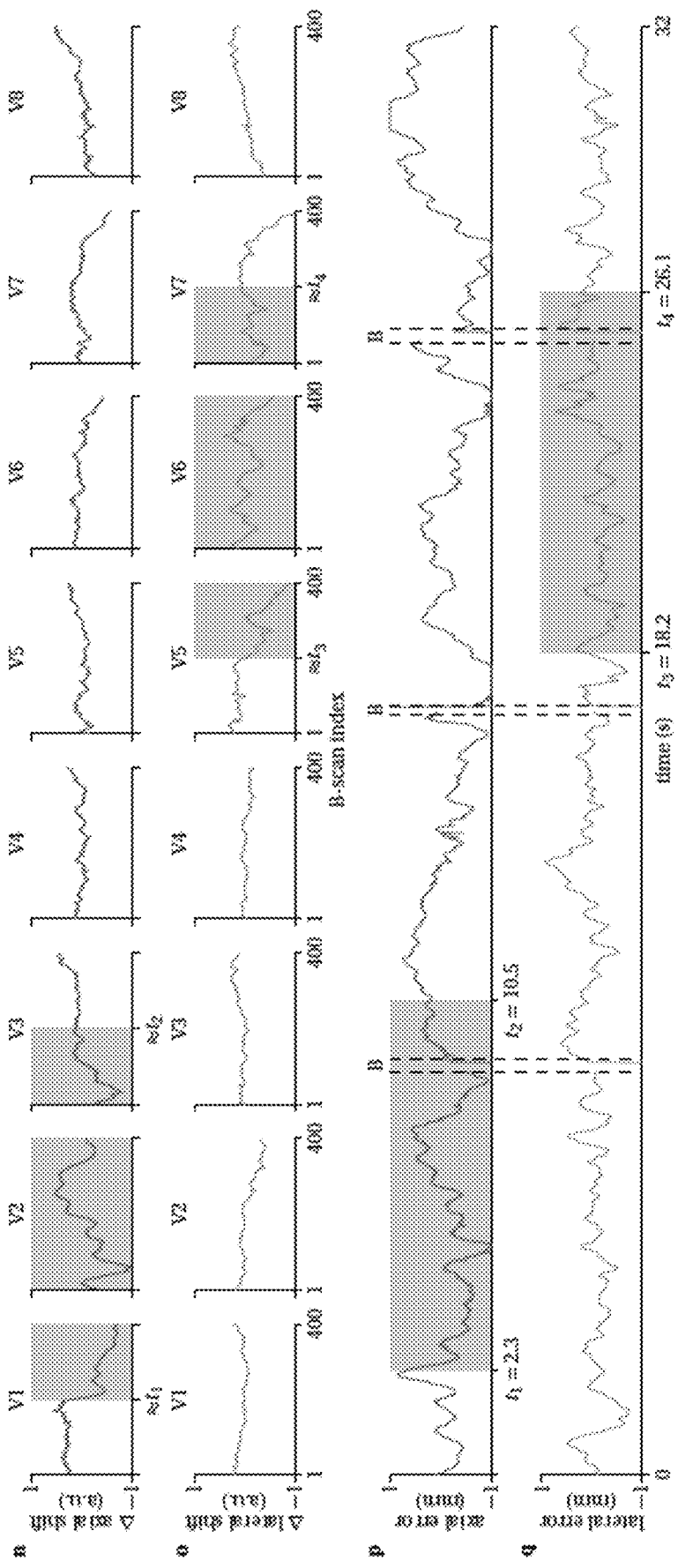
Figure 35A:
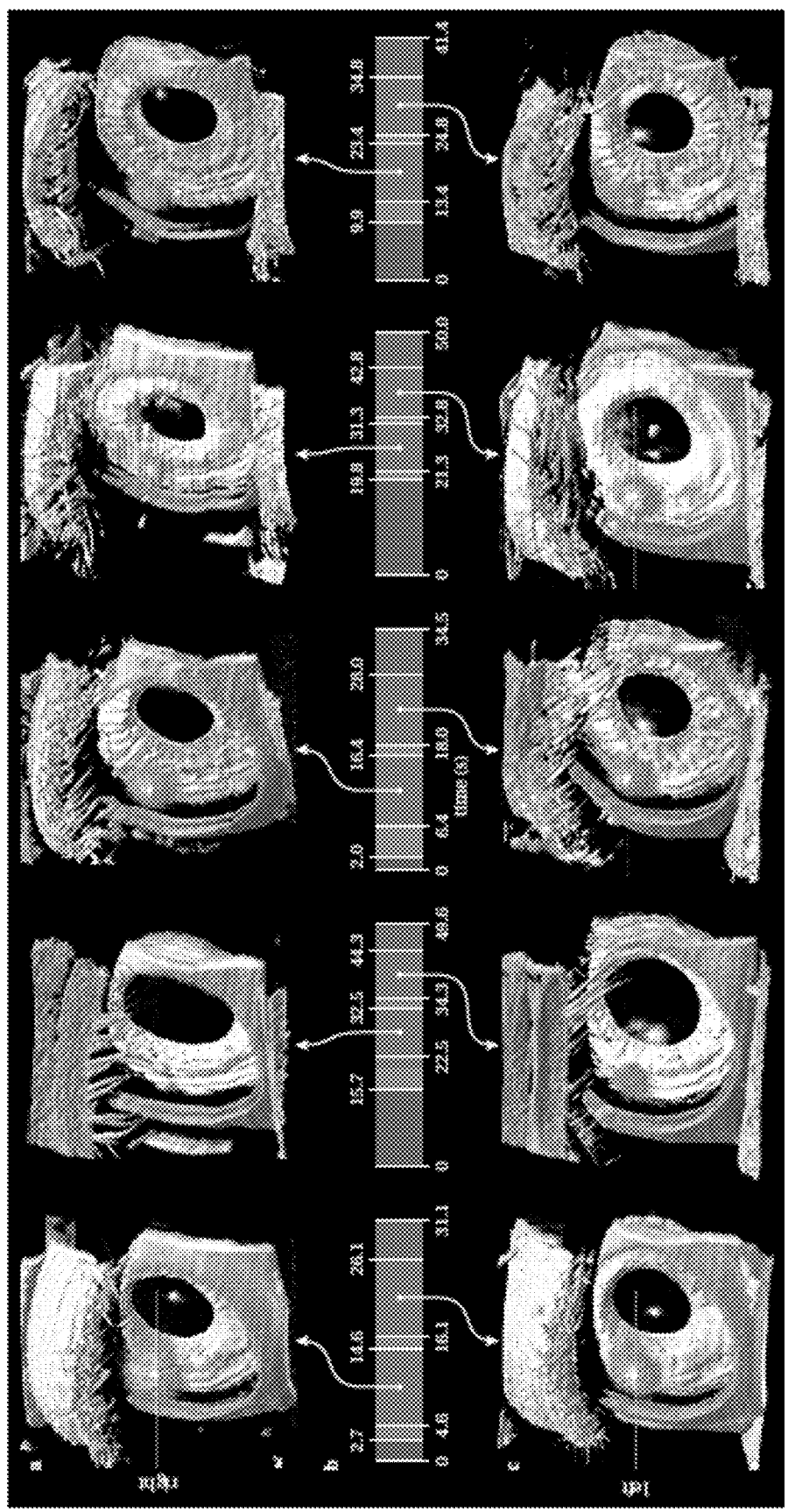
Figure 35B:
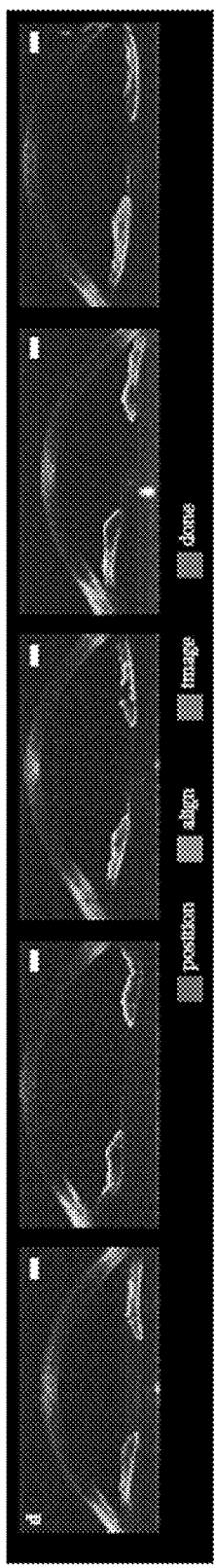
Figure 36:
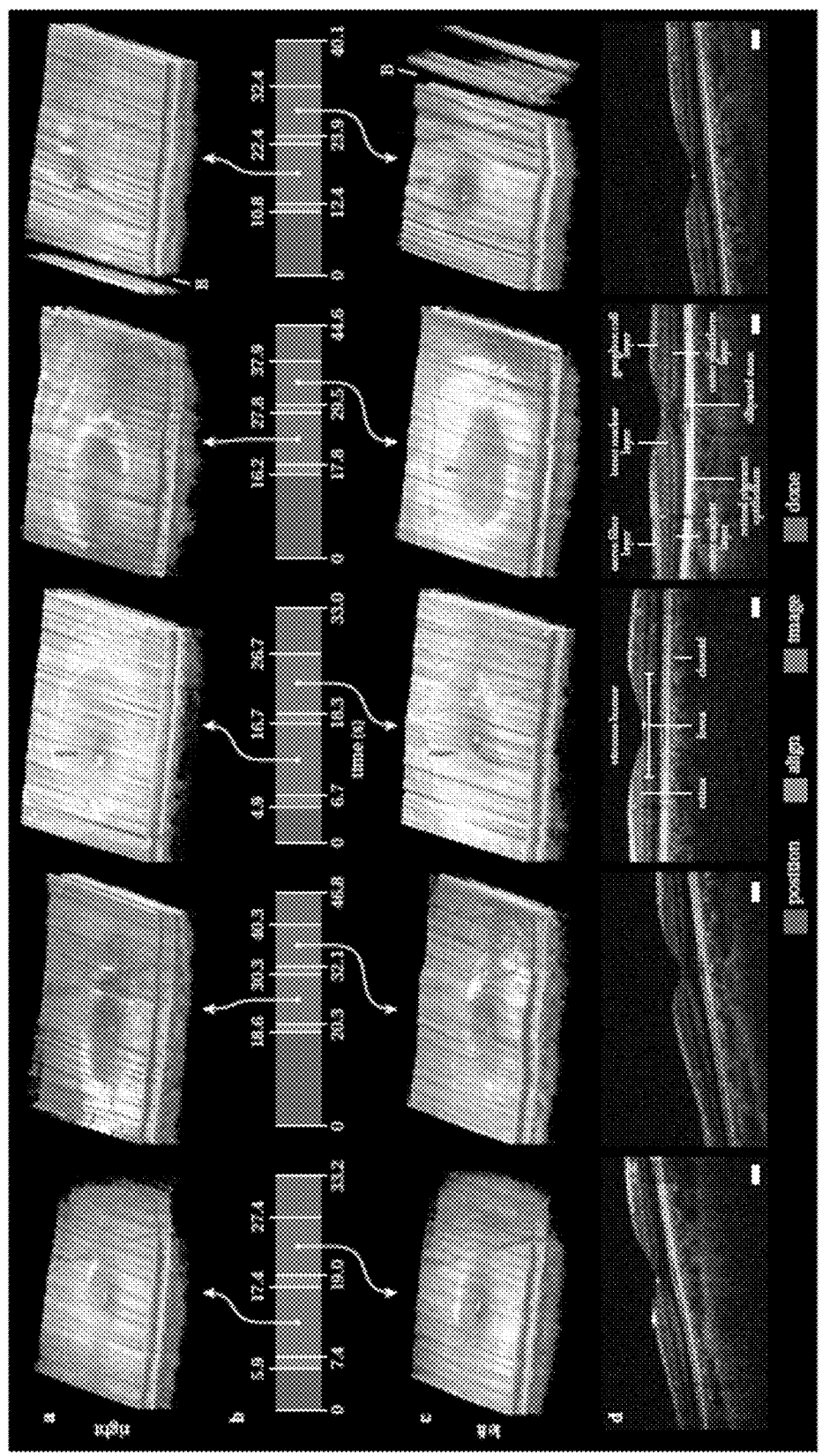

Having thus described the presently disclosed subject matter in general terms, reference will now be made to the accompanying Drawings, which are not necessarily drawn to scale, and wherein:

FIG. 1 is a block diagram of a system configured to image the eyes of a person in accordance with embodiments of the present disclosure;

FIG. 2 is a flow diagram of a method of moving a scanner to a position for imaging a target feature based on subject and feature tracking in accordance with embodiments of the present disclosure;

FIGS. 3 and 4 are a side diagram view and an image, respectively, of a system configured to image eyes of a person in accordance with embodiments of the present disclosure;

FIGS. 5A-5C are different views from a right eye tracking camera in infrared;

FIG. 6 is a controller state transition diagram for autonomous, fault-tolerant eye alignment in accordance with embodiments of the present disclosure;

FIG. 7 illustrates two different control diagrams for (a) open-loop eye tracking and for (b) closed-loop eye tracking with galvanometer/reference arm feedforward in accordance with embodiments of the present disclosure;

FIG. 8 shows (a) a Styrofoam mannequin head fitted with model eyes, (b) OCT B-scan through the model eye's center showing its anatomically realistic structures, and (c) OCT en face maximum intensity projection constructed from successive adjacent B-scans;

FIG. 9 are graphs showing accuracy test results for lateral (a) and axial (b) eye tracking with 25 mm steps and lateral (c) and axial (d) pupil tracking with 1 mm steps;

FIG. 10 are images showing step response for lateral displacement in OCT scan center position with corresponding interrupted OCT scans for each tracking mode;

FIG. 11 are images showing OCT MIPs and middle B-scans at three different model positions (columns) spaced 50 mm apart for each tracking mode (rows);

FIG. 12 are images of OCT MIPs and middle B-scans during linear pursuit for each tracking mode (rows) at different velocities (columns);

FIG. 13 are images of OCT MIPs and middle B-scans for each tracking mode when holding the mannequin with an outstretched arm to simulate physiological motion;

FIG. 14 are different images captured at different points in time during robotic scanner positioning in accordance with embodiments of the present disclosure;

FIGS. 15 and 16 are diagrams of a system including OCT engine with Mach-Zehnder topology, transmissive reference arm with adjustable length, and balanced detection in accordance with embodiments of the present disclosure;

FIG. 17 is an anterior scanner optical spot diagram for the three design wavelengths over a ±14 mm scan, indicating nearly diffraction-limited performance due to residual spherical aberration;

FIG. 18 is a retinal scanner optical spot diagram for the three design wavelengths over a ±8 degree scan, indicating nearly diffraction-limited performance due to residual spherical aberration;

FIG. 19 is a retinal scanner pupil wobble diagram indicating minimum acceptable diameter of 3.2 mm;

FIG. 20 is a perspective view and associated diagram of a system for achieving setup for accuracy and precision measurements, in which the scanner measured phantom position through a sequence of lateral and axial 1 mm steps as illustrated;

FIG. 21 is a perspective view and associated diagram of a system for setup for latency measurements;

FIG. 22 is a graph showing absolute mean error for anterior lateral steps, indicating an accuracy of 36.9 µm;

FIG. 23 is a graph showing position distribution for anterior lateral steps with per-step mean removed, indicating a precision of 1.5 µm;

FIG. 24 is a graph showing anterior galvanometer-based lateral tracking from laterally stepping a titled phantom, indicating a latency of 27.2 ms;

FIG. 25 is a graph showing absolute mean error for retinal lateral steps, indicating an accuracy of 36.6 µm;

FIG. 26 is a graph showing distribution for retinal lateral steps with per-step mean removed, indicating a precision of 1.6 µm;

FIG. 27 is a graph showing retinal fast steering mirror-based lateral tracking from laterally stepping an occluded phantom, indicating a latency of 29.8 ms;

FIG. 28 is a graph showing absolute mean error for anterior axial steps, indicating an accuracy of 32.1 µm;

FIG. 29 is a graph showing position distribution for anterior axial steps with per-step mean removed, indicating a precision of 1.9 µm;

FIG. 30 is a graph showing absolute mean error for retinal axial steps, indicating an accuracy of 63.6 µm;

FIG. 31 is a graph showing position distribution for retinal axial steps with per-step mean removed, indicating a precision of 2.4 µm;

FIG. 32 is a graph showing anterior and retinal voice coil motor axial tracking from axially stepping a phantom, indicating a latency of 24.8 ms;

FIG. 33 are graphs that show pupil alignment error power spectra from all autonomous imaging sessions;

FIG. 34A shows images of freestanding subject using the anterior scanner with high (800×800×1376 vx) and intermediate (800×400×1376 vx) density scans;

FIG. 34B shows images of sequential anterior segment 800×400×1376 vx volumes without registration during transient suspension of axial tracking for $t_1<t<t_2$ (gray) and lateral tracking for $t_3<t<t_4$ (gray);

FIG. 34C are graphs showing shifts required to register each volume from image other images;

FIGS. 35A and 35B are images of a retina acquired in accordance with embodiments of the present disclosure; and FIG. 36 are images of autonomous retinal imaging results in freestanding subjects with undilated eyes.

SUMMARY

The presently disclosed subject matter relates to systems and methods for imaging a target feature of a subject based on the tracked positions of the subject and the target feature. According to an aspect, a system includes a scanner configured to image a target feature of a subject. The system also includes a mechanism configured to move the scanner. Further, the system includes a subject tracker configured to track positioning of the subject. The system also includes a feature tracker configured to track positioning of the target feature within an area within which the target feature is positioned such that the target feature is imageable by the scanner. Further, the system includes a controller. The controller is configured to control the mechanism to move the feature tracker to a position such that the feature tracker is operable to track a position of the target feature based on the tracked position of the subject by the subject tracker. The controller is also configured to control the mechanism to move the scanner to a position such that the scanner is operable to image the target feature based on the tracked position of the target feature by the feature tracker. Further, the controller is configured to control the scanner to image the target feature.

DETAILED DESCRIPTION

The following detailed description is made with reference to the figures. Exemplary embodiments are described to illustrate the disclosure, not to limit its scope, which is defined by the claims. Those of ordinary skill in the art will recognize a number of equivalent variations in the description that follows.

Articles "a" and "an" are used herein to refer to one or to more than one (i.e. at least one) of the grammatical object of the article. By way of example, "an element" means at least one element and can include more than one element.

"About" is used to provide flexibility to a numerical endpoint by providing that a given value may be "slightly above" or "slightly below" the endpoint without affecting the desired result.

The use herein of the terms "including," "comprising," or "having," and variations thereof is meant to encompass the elements listed thereafter and equivalents thereof as well as additional elements. Embodiments recited as "including," "comprising," or "having" certain elements are also contemplated as "consisting essentially of" and "consisting" of those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a range is stated as between 1%-50%, it is intended that values such as between 2%-40%, 10%-30%, or 1%-3%, etc. are expressly enumerated in this specification. These are only examples of what is specifically intended, and all possible combinations of numerical values between and including the lowest value and the highest value enumerated are to be considered to be expressly stated in this disclosure.

Unless otherwise defined, all technical terms used herein have the same meaning as commonly understood by one of ordinary skill in the art to which this disclosure belongs.

In accordance with embodiments, disclosed herein are systems that include an active-tracking scanner that can be positioned by a robot arm. A system in accordance with embodiments of the present disclosure may include 3D cameras that are used to find a patient in space. The robot arm can articulate the scanner for grossly aligning the scanner to the patient's eye with a workspace comparable to the human arm. The system also includes scanner-integrated cameras to locate the patient's pupil. Further, active tracking components can be used to eliminate or significantly reduce mechanical head stabilization and augment the OCT acquisition in real time to optically attenuate motion artifacts.

The functional units described in this specification have been labeled as computing devices. A computing device may be implemented in programmable hardware devices such as processors, digital signal processors, central processing units, field programmable gate arrays, programmable array logic, programmable logic devices, cloud processing systems, or the like. The computing devices may also be implemented in software for execution by various types of processors. An identified device may include executable code and may, for instance, comprise one or more physical or logical blocks of computer instructions, which may, for instance, be organized as an object, procedure, function, or other construct. Nevertheless, the executable of an identified device need not be physically located together but may comprise disparate instructions stored in different locations which, when joined logically together, comprise the computing device and achieve the stated purpose of the computing device. In another example, a computing device may be a mobile computing device such as, for example, but not limited to, a smart phone, a cell phone, a pager, a personal digital assistant (PDA), a mobile computer with a smart phone client, or the like. In another example, a computing device may be any type of wearable computer, such as a computer with a head-mounted display (HMD), or a smart watch or some other wearable smart device. Some of the computer sensing may be part of the fabric of the clothes the user is wearing. A computing device can also include any type of conventional computer, for example, a laptop computer or a tablet computer. A typical mobile computing device is a wireless data access-enabled device (e.g., an iPHONE® smart phone, a BLACKBERRY® smart phone, a NEXUS ONE™ smart phone, an iPAD® device, smart watch, or the like) that is capable of sending and receiving data in a wireless manner using protocols like the Internet Protocol, or IP, and the wireless application protocol, or WAP. This allows users to access information via wireless devices, such as smart watches, smart phones, mobile phones, pagers, two-way radios, communicators, and the like. Wireless data access is supported by many wireless networks, including, but not limited to, Bluetooth, Near Field Communication, CDPD, CDMA, GSM, PDC, PHS, TDMA, FLEX, ReFLEX, iDEN, TETRA, DECT, DataTAC, Mobitex, EDGE and other 2G, 3G, 4G, 5G, and LTE technologies, and it operates with many handheld device operating systems, such as PalmOS, EPOC, Windows CE, FLEXOS, OS/9, JavaOS, iOS and Android. Typically, these devices use graphical displays and can access the Internet (or other communications network) on so-called mini- or micro-browsers, which are web browsers with small file sizes that can accommodate the reduced memory constraints of wireless networks. In a representative embodiment, the mobile device is a cellular telephone or smart phone or smart watch that operates over GPRS (General Packet Radio Services), which is a data technology for GSM networks or operates over Near Field Communication e.g. Bluetooth. In addition to a conventional voice communication, a given mobile device can communicate with another such device via many different types of message transfer techniques, including Bluetooth, Near Field Communication, SMS (short message service), enhanced SMS (EMS), multi-media message (MMS), email WAP, paging, or other known or later-developed wireless data formats. Although many of the examples provided herein are implemented on smart phones, the examples may similarly be implemented on any suitable computing device, such as a computer.

An executable code of a computing device may be a single instruction, or many instructions, and may even be distributed over several different code segments, among different applications, and across several memory devices. Similarly, operational data may be identified and illustrated herein within the computing device, and may be embodied in any suitable form and organized within any suitable type of data structure. The operational data may be collected as a single data set, or may be distributed over different locations including over different storage devices, and may exist, at least partially, as electronic signals on a system or network.

The described features, structures, or characteristics may be combined in any suitable manner in one or more embodiments. In the following description, numerous specific details are provided, to provide a thorough understanding of embodiments of the disclosed subject matter. One skilled in the relevant art will recognize, however, that the disclosed subject matter can be practiced without one or more of the specific details, or with other methods, components, materials, etc. In other instances, well-known structures, materials, or operations are not shown or described in detail to avoid obscuring aspects of the disclosed subject matter.

As used herein, the term "memory" is generally a storage device of a computing device. Examples include, but are not limited to, read-only memory (ROM) and random access memory (RAM).

The device or system for performing one or more operations on a memory of a computing device may be a software, hardware, firmware, or combination of these. The device or the system is further intended to include or otherwise cover all software or computer programs capable of performing the various heretofore-disclosed determinations, calculations, or the like for the disclosed purposes. For example, exemplary embodiments are intended to cover all software or computer programs capable of enabling processors to implement the disclosed processes. Exemplary embodiments are also intended to cover any and all currently known, related art or later developed non-transitory recording or storage mediums (such as a CD-ROM, DVD-ROM, hard drive, RAM, ROM, floppy disc, magnetic tape cassette, etc.) that record or store such software or computer programs. Exemplary embodiments are further intended to cover such software, computer programs, systems and/or processes provided through any other currently known, related art, or later developed medium (such as transitory mediums, carrier waves, etc.), usable for implementing the exemplary operations disclosed below.

In accordance with the exemplary embodiments, the disclosed computer programs can be executed in many exemplary ways, such as an application that is resident in the memory of a device or as a hosted application that is being executed on a server and communicating with the device application or browser via a number of standard protocols, such as TCP/IP, HTTP, XML, SOAP, REST, JSON and other sufficient protocols. The disclosed computer programs can be written in exemplary programming languages that execute from memory on the device or from a hosted server, such as BASIC, COBOL, C, C++, Java, Pascal, or scripting languages such as JavaScript, Python, Ruby, PHP, Perl, or other suitable programming languages.

As referred to herein, the terms "computing device" and "entities" should be broadly construed and should be understood to be interchangeable. They may include any type of computing device, for example, a server, a desktop computer, a laptop computer, a smart phone, a cell phone, a pager, a personal digital assistant (PDA, e.g., with GPRS NIC), a mobile computer with a smartphone client, or the like.

As referred to herein, a user interface is generally a system by which users interact with a computing device. A user interface can include an input for allowing users to manipulate a computing device, and can include an output for allowing the system to present information and/or data, indicate the effects of the user's manipulation, etc. An example of a user interface on a computing device (e.g., a mobile device) includes a graphical user interface (GUI) that allows users to interact with programs in more ways than typing. A GUI typically can offer display objects, and visual indicators, as opposed to text-based interfaces, typed command labels or text navigation to represent information and actions available to a user. For example, an interface can be a display window or display object, which is selectable by a user of a mobile device for interaction. A user interface can include an input for allowing users to manipulate a computing device, and can include an output for allowing the computing device to present information and/or data, indicate the effects of the user's manipulation, etc. An example of a user interface on a computing device includes a graphical user interface (GUI) that allows users to interact with programs or applications in more ways than typing. A GUI typically can offer display objects, and visual indicators, as opposed to text-based interfaces, typed command labels or text navigation to represent information and actions available to a user. For example, a user interface can be a display window or display object, which is selectable by a user of a computing device for interaction. The display object can be displayed on a display screen of a computing device and can be selected by and interacted with by a user using the user interface. In an example, the display of the computing device can be a touch screen, which can display the display icon. The user can depress the area of the display screen where the display icon is displayed for selecting the display icon. In another example, the user can use any other suitable user interface of a computing device, such as a keypad, to select the display icon or display object.

As referred to herein, an OCT scanner may be any device or system configured to use low-coherence light to capture micrometer-resolution, two- and three-dimensional images from within optical scattering media. For example, OCT scanners may be used for medical imaging and industrial nondestructive testing. In a particular example, an OCT scanner may be used for imaging a retina of a patient's eye for diagnosing a medical condition of the patient.

FIG. 1 illustrates a block diagram of a system 100 configured to image the eyes of a person 102 in accordance with embodiments of the present disclosure. For ease of illustrates, only a side view of the person's 102 head and right eye 104 are shown. In this example, the eye 104 is considered a target feature of the subject (i.e., the person's 102 face) for imaging by an OCT scanner 106. In this example, the OCT scanner 106 may be configured to non-invasively capture images the eye's anterior segment or retina. Alternatively, for example, the target feature may be any other feature of a subject that is desired to be imaged in accordance with embodiments of the present disclosure. The system 100 may include a mechanism 108 configured to move the OCT scanner 106. For example, the mechanism 108 may be a robotic arm configured to move upwards, downwards, and/or side-to-side (i.e., along the x-, y-, z-axes) such that it can position and orient the OCT scanner 106 in a suitable position and orientation for capturing images of the anterior segment or retina of the eye 104. In addition, the robotic arm may rotate the scanner suitably about a pivot 110 such that the OCT scanner 106 is properly oriented for capturing images of the eye's 104 retina or another target feature.

A controller 110 may be operatively connected to the mechanism 108 (e.g., robotic arm) for controlling the movement of the mechanism 108 to move the OCT scanner 106 to a position in accordance with embodiments of the present disclosure. The controller 110 may be a part of or a separate device that is operatively connected to a computing device 112. The computing device 112 may communicate control commands to the controller 110 for operating the mechanism 108 in accordance with embodiments of the present disclosure. The computing device 112 may be a desktop computer, a laptop computer, a tablet computer, a smartphone, or any other suitable computing device having hardware, software, firmware, or combinations thereof for implementing the functionality described herein. The controller 110 may having hardware, software, firmware, or combinations thereof for implementing the functionality described herein. As an example, the controller 110 and the computing device 112 may each include one or more processors and memory for implementing the functionality described herein. The controller 110 and the computing device 112 may also each have input/output (I/O) modules for enabling these devices to communicate with each other and other suitable devices.

The system 100 includes a subject tracker 114 and a feature tracker 116 for use in tracking the person 102 generally and also the eye 104. Particularly, the subject tracker 114 is configured to track positioning of the person 102 (i.e., the subject). The feature tracker 116 is configured to track positioning of the eye 104 (i.e., the target feature of the subject) within an area within which the eye 104 is positioned such that the eye 104 is imageable by the OCT scanner 106. The controller 110 may be operatively connected to the subject tracker 114 and the feature tracker 116 either directly or via the computing device 112 as shown. The controller 110 may receive the tracked position information from both the subject tracker 114 and the feature tracker 116. Based on the received tracked position person 102 by the subject tracker 114, the controller 110 may control the mechanism 108 to move the feature tracker 116 to a position such that the feature tracker 116 is operable to track a position of the target feature based on the tracked position of the person 102 by the subject tracker 114. The controller 110 may also control the mechanism 108 to move the OCT scanner 106 to a position such that the scanner is operable to image the eye 104 (or specifically the eye's 104 retina) based on the tracked position of the eye 104 by the feature tracker 116. Subsequent to and while in a suitable position to image the eye's 104 retina, the controller 110 may control the OCT scanner 106 to image the eye's 104 retina.

FIG. 2 illustrates a flow diagram of a method of moving a scanner to a position for imaging a target feature based on subject and feature tracking in accordance with embodiments of the present disclosure. The method of FIG. 2 is described by example as being implemented by the system 100 shown in FIG. 1, but it should be understood that the method may alternatively be implemented by any other suitable system. Further, it is noted that the computing device 112 may be operatively connected to one or more user interfaces 118 (e.g., a display such as a touchscreen display, a mouse, a keyboard, a speaker, a trackpad, etc.) for receiving input from a user (e.g., an operator of the OCT device, or the person 102) and for presenting information to the user. The user may interact with the user interface(s) 118 for inputting a request for the method to commence. Information that the user may input includes, but is not limited to, identification of the user, medical information, payment information, etc.

Referring to FIG. 2, the method includes receiving 200 a command to capture an OCT image of a person's eye. For example referring to FIG. 1, a user, such as the person 102 or an OCT device operator, may input a command into the user interface(s) 118 for initiating steps for capturing OCT images of the person's 102 retina. For example, the user may use a keyboard, keypad, or button to initiate the image capture process. The command may be communicated by the user interface(s) 118 to the computing device 112.

The method of FIG. 2 includes tracking 202 positioning of the person. Continuing the aforementioned example, the subject tracker 114 may track a position of the person 102. For example, the subject tracker 114 may include one or more cameras directed towards an area where a subject can be expected to be positioned to await imaging. In this example, a floor may be marked to indicate to the person 102 where to stand for eye imaging. Signage or other indicators may inform the person to face in a direction towards the scanner 106. The camera(s) of the subject tracker 114 may be directed to an area above the flooring markings where the person's 102 face can be expected to be located. The subject tracker 114 may track the face of the person 102 and provide tracking data (e.g., position data of the tracked face) to the controller 110.

The method of FIG. 2 includes presenting 204 the person with positioning feedback information. Continuing the aforementioned example, the computing device 112 may control the user interface(s) 118 to present to the person 102 or another assisting the person information on adjusting the person's 102 positioning such that the eye 104 of the person 102 is in an area where the feature tracker 116 can track the pupil of the eye 104. For example, a speaker of the user interface(s) 118 may be controlled to emit auditory instruction to the person 102 to move forward in order to be in close enough proximity for the feature tracker 116 to track the eye's 104 pupil. Alternatively, for example, the user interface(s) 118 may instruct the person 102 to make other movements, such as tilting his or her head, moving to one side or another, backing up, in order to be in a proper area for the eye's 104 pupil to be tracked. Further, alternative to auditory instruction by a speaker, a display or other suitable user interface may be used to present instruction to the person 102.

The method of FIG. 2 includes determining 206 whether the person is positioned within a predetermined position for pupil tracking. Continuing the aforementioned example, the controller 110 may use positioning information from the subject tracker 114 to determine whether the person 102 is in position for the eye's pupil to be tracked by the feature tracker 116. In response to determining that the person is within the predetermined position for pupil tracking, the method may proceed to step 208. Otherwise in response to determining that the person is not within the predetermined position for pupil tracking, the method may proceed to step 204 such that positioning feedback information may be presented to the person to adjust positioning such that the pupil can be tracked.

The method of FIG. 2 includes controlling 208 a mechanism to move an OCT scanner 106 to a position for initiating imaging of the person's retina. Continuing the aforementioned example, the controller 110 may control the mechanism 108 (e.g., robotic arm) to move the OCT scanner 106 to a position such that the OCT scanner 106 can image the retina of the eye 104.

The method of FIG. 2 includes tracking 210 positioning of a pupil of the person's eye. Continuing the aforementioned example, the feature tracker 116 may track a pupil of the eye 104. In an example, the feature tracker 116 may include one or more cameras configured to track a pupil of the person's eye 104 when in a field-of-view (FOV) of the camera(s) of the feature tracker 116. The positioning information generated by the camera(s) may be suitably processed by the feature tracker 116 and output to the controller 110. The controller 110 can use the positioning information to control the mechanism 108 to adjust positioning of the OCT scanner 106 as may be needed such that the OCT scanner 106 can image the retina. For example, subsequent to initiation of imaging by the OCT scanner 106, the person's eye 104 may slightly move such that the OCT scanner 106 needs position adjustment to compensate for the person's movement in order to properly image the retina. The method includes moving 212 the OCT scanner in response to movement of the person's pupil. For example, the controller 110 may be configured to control the mechanism 108 to move the OCT scanner 106 in response to movement of the person's 102 pupil such that the retina can be properly imaged as described in further detail herein.

The method of FIG. 2 includes controlling 214 the OCT scanner to image the person's retina. Continuing the aforementioned example, the controller 110 can control the OCT scanner 106 to image the retina. The retina image data may be output to the computing device 112 for storage in memory and further image processing. Alternative to the controller 110 directly controlling the OCT scanner for imaging, the computing device 112 may be considered as a controller and may be directly connected to the OCT scanner 106 for controlling the OCT scanner to image the retina. The imaging data of the retina may subsequently be processed and sent to the computing device 112 for further processing and storage.

In accordance with embodiments, FIGS. 3 and 4 illustrate a side diagram view and an image, respectively, of a system 300 configured to image eyes of a person 302. For ease of illustration in FIG. 3, only a front portion of the person's 302 head is shown. With reference to FIG. 3, the person 302 is positioned facing the system 300 such that a right eye 304 of the person 302 can be imaged. The system 300 in this example is a robotically-aligned OCT scanner that can perform eye and pupil tracking. The system 300 can include a controller (not shown) that may implement multiple different tracking modes. One mode may be referred to as an "eye" mode that uses an eye tracker. Another mode may be referred to as a "pupil" mode that uses a pupil tracker once the scanner is roughly aligned. Another mode may be referred to as a "pupil+aiming" mode that uses the pupil tracker with error feedforward for scan aiming.

With reference to FIGS. 3 and 4, the system 300 includes three subsystems. One subsystem includes fixed-base eye tracking cameras 400 and 402, which may also be referred to as a left depth camera and a right depth camera, respectively (only shown in FIG. 4). Cameras 400 and 402 may be configured to track the person 302. Another subsystem of the system 300 is an OCT scanner 306 with integrated pupil tracking cameras 308 and 310 mounted on a robot arm 312. Another subsystem includes an OCT engine with a motorized reference arm which enables the scanner to appropriately image eye features at variable distance from the scanner. For eye tracking (or "subject tracking"), the cameras 402 and 402 may be RealSense D415 RGB-D cameras (available from Intel, Santa Clara, California), one for each eye, positioned symmetrically about the robot arm 312 and aimed at the tracking workspace where a person for imaging may be located. These vantage points were chosen to obtain clear views of the designated eye (left eye for left camera and right eye for right camera), even with the scanner partially occluding the face during alignment. Each camera's position in the robot's coordinate system may be calibrated by imaging a target mounted on the robot end-effector. An LED light above each camera may be used for uniform, flicker-free illumination.

For OCT imaging, a custom anterior eye OCT scanner with integrated pupil tracking cameras may be used. This type of OCT scanner is shown in FIG. 3 as an example. The scanner 306 and inline pupil camera 310 share a 2 inch objective lens with a 93 mm working distance to provide a comfortable separation for patients during automatic alignment. Suitable galvanometers 314 may be used, such as the Saturn 1B galvanometers (available from Pangolin Laser Systems; Orlando, Florida) with a 3.8 mm beam launched from a reflective collimator. A dichroic with a 700 nm cutoff folded the scanner 306 into the inline pupil camera's 310 optical path. The optical design is configured to achieve diffraction-limited OCT performance at 1060 nm over a ±15 mm field of view. Further, the scanner's backbone may be suitably made and configured (e.g., by 3D printing) to position all components in accordance with the optimization results. This yielded a theoretical lateral OCT resolution of 43 µm. The OCT field of view was co-registered to the inline pupil camera 310 using galvanometer voltage offsets. The offset pupil camera 308 can create a stereo pair for pupil depth estimation. In experiments, a Blackfly S 04S2M camera and a Blackfly 13E4C camera (FLIR; Richmond, BC, Canada) were used for the inline pupil camera 310 and the offset pupil cameras 308, respectively. A ring light was mounted on the objective lens housing to provide uniform illumination and eliminate shadows under the eyebrow for pupil tracking. The robot arm 312 may be an ABB Robotics arm available from ABB Robotics of Zurich, Switzerland. The robot arm 312 may be controlled at 250 Hz through its externally guided motion interface for scanner positioning.

In experiments, the scanner was operated with a custom-built swept-source OCT engine. The OCT engine used a 1060 nm swept frequency source (Axsun Technologies; Billerica, MA) with 100 nm bandwidth at a 100 kHz A-scan rate and an ALSQ150D-E01 linear stage (available from Zaber Technologies of Vancouver, BC, Canada) to adjust the reference arm length. The optical signal detection chain used a 800MSs-1 digitizer (AlazarTech; Quebec, Canada) to measure the output of a balanced photoreceiver (available from Thorlabs of Newton, New Jersey). The engine provided an imaging depth of up to 7.4 mm, suitable for imaging the complete anterior chamber. OCT volumes were acquired at 0.3 Hz using a 512×1376×512 voxel raster scan pattern which had physical dimensions of 12×7.4×12 mm. Galvanometer aiming offsets were generated using a NI-9263 analog output module (available from National Instruments of Austin, Texas) and added to the engine's scan waveforms by a custom summing circuit. The adjustable reference arm and galvanometer offsets enabled the aiming portion of the pupil+aiming mode. Real-time OCT processing and rendering on the graphics processing unit were performed with custom software.

In accordance with embodiments, the eye's 3D position in the robot's coordinate system may be tracked by identifying a face of the person in the RealSense D415 camera's left stereo image using OpenFace 2.0 in video tracking mode. As an example, FIGS. 5A-5C are different views from the right eye tracking camera in infrared. Particularly, FIGS. 5A and 5B show infrared depth and colorized depth, respectively. FIG. 5C shows the detected pupil overlay. By manually tuning the exposure and illumination, left stereo images suitable for face tracking can be acquired despite the presence of the D415 camera's active stereo texture, without compromising depth imaging. Because the D415 cameras can generate depth images from the left stereo viewpoint, detected facial landmarks were thus also valid in the depth image without the need for reprojection. The eye's 3D position may be estimated or determined by computing the mean position of all depth pixels bounded by the facial landmarks for the eye of interest. In experiments, eye tracking operated at approximately 38 fps for the right and left eye tracking cameras together for input images sized 848×480 pixels.

The pupil's 3D position in the inline pupil camera's coordinate system may be tracked by triangulating the pupil seen in multiple cameras. The pupil in the inline pupil camera's view can be identified by adaptively thresholding the image and finding the largest connected component (CC) with a roughly square aspect ratio. The pupil's pixel position can be estimated or determined as that CC's bounding box center, because the CC frequently did not include the entire pupil interior and thus biased the CC's centroid away from the true center. The ray may be projected from the inline pupil camera through the pupil center onto the offset pupil camera's image and a line search for the pupil may be performed. This can yield the pupil position in 3D space relative to the scanner. Inline pupil camera processing operated at 230 fps whereas offset pupil camera processing operated at 140 fps due to a hardware framerate limitation. The two cameras' framerates can be matched using a zero-order hold. Alternatively, the pupil position in 3D space relative to the scanner may be computed by triangulation directly without a line search when two or more cameras image the pupil.

In accordance with embodiments, a controller, such as the controller 110 shown in FIG. 1, can perform alignment in accordance with a two-stage, high-level technique. In a first stage, the controller may position the scanner 306 to bring the desired eye 304 into the inline pupil camera's 310 field of view using the coarse eye position from the fixed-base eye tracking cameras 400. In a second stage, once the inline pupil camera reports or determines pupil detection, the controller may position the scanner exclusively using the fine eye position from pupil tracking. Advantageously, for example, this technique can enable a large workspace without compromising fine alignment.

FIG. 6 illustrates a controller state transition diagram for autonomous, fault-tolerant eye alignment in accordance with embodiments of the present disclosure. This is a state machine that can implement selectively engaged eye and pupil tracking as well as tolerated tracking failures for both. If eye tracking failed, either because no patient was present or because the scanner occluded the patient's face, the robot moved the scanner to a "recovery" position at state (a) to prevent occlusions. If pupil tracking failed or the estimated pupil position deviated significantly from the scanner's current position, the robot tracked only the coarse eye position at state (b). The deviation check prevented incorrectly tracking the wrong eye, for instance, if the pupil camera passed over the left eye while the robot moved to position the scanner to view the right eye. Otherwise, the scanner relied on pupil tracking at (c) for fine alignment.

FIG. 7 illustrates two different control diagrams for (a) open-loop eye tracking and for (b) closed-loop eye tracking with galvanometer/reference arm feedforward. Referring to FIG. 7, EP represents eye position, PT represents pupil tracker, RC references robot controller, SP represent scanner position, and G/SO represent galvanometer/stage offset. The controller can apply distinct control techniques for the eye and pupil tracking states. During eye tracking, the controller can issue open-loop position setpoints $\vec{r}_n$ to the robot arm at (a) after smoothing the eye position $\vec{e}_n$ with an m-sample moving average filter, $$\vec{r}_n = C_R \cdot \left( \frac{1}{m} \sum_{i=0}^{m-1} \vec{e}_{n-i} \right) + \vec{C}_t,$$

where C is the camera pose and m=15, although other suitable values may be chosen depending upon the specific application. No feedback was possible because the scanner position did not affect the estimated eye position except in the undesired case of face occlusion. During pupil tracking, the controller implemented a feedback loop to eliminate the tracking error $\vec{p}$ because the pupil cameras were referenced to the robot arm at (b). The controller applied proportional gain $k_p$ to drive the robot arm's position setpoints, $$\vec{r}_n = \hat{\vec{r}}_{n-1} + k_p \vec{p}_n$$

where $\hat{\vec{r}}$ is the robot arm's actual position and $k_p$=0.4, although other suitable values may be chosen depending upon the specific application, and fed the error signal forward as a galvanometer scan offset and motorized reference arm setpoint (i.e., "aiming" in the pupil+aiming mode). While the robot tracked the eye with "low" bandwidth, the galvanometers and reference arm stage rapidly corrected the residual error with "high" bandwidth. This low bandwidth tracking centered the galvanometers and reference arm within their operating range to ensure the availability of high bandwidth tracking except for large eye motion.

For all robot motions, the controller can generate time optimal trajectories in Cartesian space each control cycle (4 ms) to bring the scanner to its desired position. A maximum velocity of 100 mm or any other suitable velocity can be set in each dimension to avoid startling patients.

In experiments, an evaluation of the system was performed using a Styrofoam mannequin head fitted with Okulo GR-6 model eyes (BIONIKO; Miami, FL) that included an anatomically realistic cornea, iris, and anterior chamber. FIG. 8 shows (a) a Styrofoam mannequin head fitted with model eyes; (b) OCT B-scan through the model eye's center showing its anatomically realistic structures; and (c) OCT en face maximum intensity projection constructed from successive adjacent B-scans (the scale bars are 1 mm). Mannequins were selected over human subjects for testing because doing so provided the necessary standardization and precision. Successful alignment was considered according to clinical OCT imaging practice: laterally center the pupil and axially position the corneal apex near zero OCT depth. These tests evaluated performance aligning stationary eyes, pursuing moving eyes, and tracking eyes exhibiting common physiologic motions. Except for tracking accuracy and precision assessments, we performed all tests in the three possible tracking modes: eye, pupil, and pupil+aiming. Testing in this way elicited the effect of each successive technique.

Both eye and pupil tracking were examined to determine their accuracy and precision. For eye tracking, the mannequin was positioned near the tracking workspace center facing the robot arm without the scanner. Then the head was moved laterally and axially in steps of 25 mm using a linear stage. Tracking precision was calculated using the standard deviation of the estimated eye position at each step. Tracking accuracy was calculated using the standard deviation of the error in estimated position displacement. For pupil tracking, we manually aligned the mannequin's left eye with the scanner. Subsequently, the same measurements were performed as with eye tracking above but using 1 mm steps.

To assess the controller's ability to obtain consistent OCT volumes of stationary eyes, alignment was performed with the mannequin's left eye at three different positions spaced 50 mm apart. Each attempt started from the recovery position. The time to alignment was recorded and acquired an OCT volume at 512×1376×512 voxels once alignment had stabilized. Additionally, the system's tracking step response was elicited by rapidly shifting the eye laterally by approximately 5 mm using a linear stage midway through an OCT volume acquisition. The scanner position and pupil tracking error was recorded during the response, as well as the interrupted OCT volume.

Table 1 below shows tracking position and accuracy.

| Metric | Right Eye Tracking (µm) | | Left Eye Tracking (µm) | | Pupil Tracking (µm) | |
| --- | --- | --- | --- | --- | --- | --- |
| | Lateral | Axial | Lateral | Axial | Lateral | Axial |
| Precision | 130 | 82 | 130 | 100 | 6.3 | 64 |
| Accuracy | 280 | 580 | 310 | 840 | 12 | 170 |

To assess the controller's ability to obtain OCT volumes of moving eyes, automatic alignment was performed while the mannequin's left eye was moved at 10 mm, 20 mm, and 30 mm on a linear stage for 150 mm. While the system's intended use case does not include pursuit of eyes moving so rapidly for such a distance, this test served to demonstrate performance for extreme patient motion. The scanner position, pupil tracking error, and continuous OCT volumes were recorded at 512×1376×512 voxels (0.3 Hz) during the pursuit. All tests started with the system initially aligned to the eye.

To assess the controller's ability to obtain OCT images of eyes undergoing physiologic movement, the mannequin head was held with an outstretched arm within the tracking workspace. This allowed physiologic motions such as tremor, pulse, and respiration to propagate to the mannequin.

A set of OCT volumes was recorded at 512×1376×512 voxels (0.3 Hz) once alignment had initially stabilized.

Table 1 above and FIG. 9 show the results of the tracking precision and accuracy evaluation. Particularly, regarding FIG. 9, this figure illustrates graphs showing accuracy test results for lateral (a) and axial (b) eye tracking with 25 mm steps and lateral (c) and axial (d) pupil tracking with 1 mm steps. The eye trackers demonstrated sub-millimeter accuracy whereas the pupil tracker demonstrated 12 μm lateral and 170 μm axial accuracy.

FIG. 10 are images showing step response for lateral displacement in OCT scan center position (i.e., robot position+galvanometer offset) with corresponding interrupted OCT scans for each tracking mode. Further, FIG. 10 shows the step response of the system using each tracking mode. The robot exhibited a control lag of approximately 50 ms. Using rise times (10% to 90%) to estimate bandwidth, the tracking modes exhibited 1.1 Hz and 9.7 Hz lateral response bandwidth with and without aiming, respectively. The numbers of B-scans before alignment reestablished were 90, 60, and 13 for the eye, pupil, and pupil+aiming modes, respectively. At 6.4 ms per B-scan, this corresponded to 576 ms, 384 ms, and 83.2 ms settling times, respectively.

FIG. 11 are images showing OCT MIPs and middle B-scans at three different model positions (columns) spaced 50 mm apart for each tracking mode (rows). Particular, FIG. 11 shows repeated OCT B-scans and en face maximum intensity projections (MIPs) of the same eye for different model positions using each tracking mode. Each alignment completed in under 15 s which included scanner advancement, volume acquisition time of approximately 3 s, and scanner retraction. Eye tracking alone failed to stably center on the pupil whereas pupil tracking without aiming was sufficient to do so.

FIG. 12 are images of OCT MIPs and middle B-scans during linear pursuit for each tracking mode (rows) at different velocities (columns). Particularly, FIG. 12 shows the best (i.e., brightest with least motion artifact) OCT B-scans and MIPs obtained during the linear pursuit tests. Pupil tracking yielded usable scans at 10 mm, despite suboptimal axial alignment. Pupil tracking with aiming yielded usable scans at all three velocities.

FIG. 13 are images of OCT MIPs and middle B-scans for each tracking mode (columns) when holding the mannequin with an outstretched arm to simulate physiological motion. Particularly, FIG. 13 shows the best of four successive OCT scans obtained during the physiologic motion test using each tracking mode. Only pupil tracking with aiming obtained a reasonable OCT scan, despite the presence of high frequency lateral noise.

Advantageously, for example, systems and methods disclosed herein can be used to eliminate the need of a tabletop OCT scanner for motion suppression: mechanical head stabilization with chinrests and forehead braces. A scanner that is not designed to actively track the subject's eye and aim the scan in real time to compensate for movement in accordance with embodiments of the present disclosure may be unlikely to yield acceptable volumes. This is especially the case when performing high density volumetric acquisitions with point-scan swept-source OCT (SS-OCT), a next-generation OCT modality for both angiographic and structural imaging. For example, a 15×15 mm volume to scan the entire cornea at 20×20 m lateral resolution (750 A-scan/B-scan, 750 B-scan/volume) can require over 5 seconds to complete with a 100 kHz swept-source laser. Systems and methods in accordance with embodiments disclosed herein provide both anterior and retinal scanners with active tracking capabilities and a suitable working distance (>8 cm) for robotic imaging of human subjects. FIG. 14 are different images captured at different points in time during robotic scanner positioning in accordance with embodiments of the present disclosure. Particularly, in FIG. 14, the robotic scanner is shown positioning to approach the subject, align with the right and left eyes, and retract once done. Further, in FIG. 14, the robot arm follows the subject to keep the eye centered within the working range for optical active tracking. The scanner shown in FIG. 14 was mounted on a robot arm with 100 μm repeatability for gross positioning.

FIGS. 15 and 16 illustrate diagrams of a system including OCT engine with Mach-Zehnder topology, transmissive reference arm with adjustable length, and balanced detection in accordance with embodiments of the present disclosure. Referring to FIG. 15, a retroreflector is mounted on the voice coil motor to provide high-bandwidth changes in path length for axial active tracking. In FIG. 15, BD refers to a balanced detector; FC refers to a fiber coupler; PC refers to a polarization controller; RC refers to a reflective collimator; RR refers to a retroreflector; VCM refers to a voice coil motor.

Now referring to FIG. 16, the figure shows an anterior scanner model and optical ray trace, showing a telecentric scan with a 93 mm working distance. Lateral active tracking is achieved by altering the galvanometer scan angles, which shifts the scan laterally. For optical motion correction, three pupil cameras were used in the horizontal plane, one of which shared the OCT objective to obtain a lateral view coincident with the OCT scan. By identifying and triangulating the pupil using two or three cameras, the eye's relative position to the scanner can be recovered and used to drive the active tracking elements in the scanner to compensate at high speed.

For the anterior segment, a telecentric scanner with a 93 mm working distance is disclosed as shown in FIG. 16. In this telecentric design, lateral tracking was performed by offsetting the galvanometer angular scan waveform to yield a linear shift. In optical simulation, the design achieved a 28×28 mm maximum lateral field of view and theoretical lateral resolution of 43 nm. For example, FIG. 17 is an anterior scanner optical spot diagram for the three design wavelengths over a ±14 mm scan, indicating nearly diffraction-limited performance due to residual spherical aberration. The Airy radius is 43 micrometers. The scanner was operated with a 7.5 mm scan, which was sufficient to cover the limbus while affording 6.5 mm of lateral aiming range. For the retina, a retinal scanner was provided using a conventional 4f configuration with a 100 mm working distance and a fast steering mirror (FSM) in the retinal conjugate plane. As an example, FIG. 18 is a retinal scanner optical spot diagram for the three design wavelengths over a ±8 degree scan, indicating nearly diffraction-limited performance due to residual spherical aberration. The Airy radius is 8.5 micrometers for the entrance beam diameter of 2.5 mm. In contrast to anterior imaging where the scan pattern is translated in response to lateral motion, retinal lateral tracking was performed by introducing scan tilt at the FSM. For this design, this tilt applied a lateral shift to the pupil pivot, by which the retinal scan was aimed into the eye; otherwise, the image is partially lost if the scan clips on the iris. In optical simulation, the design achieved an 16×16° maximum field of view at the cornea and a theoretical lateral resolution of 8.5 μm, using the Navarro eye model. For example, FIG. 19 is a retinal scanner pupil wobble diagram indicating minimum acceptable diameter of 3.2 mm (dashed black line). The FSM provided up to ±5 mm lateral aiming range before vignetting at the objective lens. By filling the entire objective with the OCT scan, a retinal field of view was obtained that is sufficient to encompass the parafoveal region. The minimum pupil diameter is appropriate for both scotopic and mesocopic illumination conditions. Both scanners were driven with a SS-OCT engine (see FIG. 15) with ideal 5.4 nm axial resolution in air and 7.4 mm imaging depth. The engine used a 100 kHz swept-source laser centered at 1050 nm with 100 nm spectral bandwidth. The reference arm included a voice coil motor (VCM) in the reference arm for axial tracking of ±6 mm.

The active tracking capabilities of our anterior and retinal scanners were characterized in phantoms to determine their performance bounds. Unfortunately, quantitative tracking characterization in humans can be difficult because another tracking modality may be needed to serve as a gold standard. Instead, phantoms were selected to allow careful control of experimental conditions in evaluating accuracy, precision, and latency. Separate testing was done for the anterior and retinal scanners because they required individual calibrations and therefore could exhibit different behavior. For accuracy and precision, a pupil phantom was affixed on a motorized micrometer stage and separately advanced axially and laterally in 1 mm increments. For example, FIG. 20 illustrates a perspective view and associated diagram of a system for achieving setup for accuracy and precision measurements, in which the scanner measured phantom position through a sequence of lateral and axial 1 mm steps as illustrated. This yielded anterior scanner accuracy of 36.9 μm laterally (see FIG. 21, which illustrates a perspective view and associated diagram of a system for setup for latency measurements, in which the scanner actively tracked the phantom during single lateral 2 mm and axial 1 mm steps as shown) and 32.1 m axially and a retinal scanner accuracy of 36.6 μm laterally (and 63.6 μm axially. Similarly, the anterior precision was 1.5 μm laterally and 1.6 μm axially, and the retinal precision was 1.9 μm laterally and 2.4 μm axially.

FIG. 22 is a graph showing absolute mean error for anterior lateral steps, indicating an accuracy of 36.9 μm. FIG. 23 is a graph showing position distribution for anterior lateral steps with per-step mean removed, indicating a precision of 1.5 μm. FIG. 24 is a graph showing anterior galvanometer-based lateral tracking from laterally stepping a titled phantom, indicating a latency of 27.2 ms. Due to the phantom's tilt, a lateral step produces a change in axial position (inset) until active tracking recenters the A-scan. FIG. 25 is a graph showing absolute mean error for retinal lateral steps, indicating an accuracy of 36.6 μm. FIG. 26 is a graph showing distribution for retinal lateral steps with per-step mean removed, indicating a precision of 1.6 μm. FIG. 27 is a graph showing retinal fast steering mirror-based lateral tracking from laterally stepping an occluded phantom, indicating a latency of 29.8 ms. Due to the spot occlusion, a lateral step produces an increase in OCT A-scan brightness (inset) until activate tracking recenters the A-scan. FIG. 28 is a graph showing absolute mean error for anterior axial steps, indicating an accuracy of 32.1 μm. FIG. 29 is a graph showing position distribution for anterior axial steps with per-step mean removed, indicating a precision of 1.9 μm. FIG. 30 is a graph showing absolute mean error for retinal axial steps, indicating an accuracy of 63.6 μm. FIG. 31 is a graph showing position distribution for retinal axial steps with per-step mean removed, indicating a precision of 2.4 μm. FIG. 32 is a graph showing anterior and retinal voice coil motor axial tracking from axially stepping a phantom, indicating a latency of 24.8 ms.

For latency, the active tracking response time was assessed to eliminate a lateral and axial step disturbance. Using repeated A-scans at the same target position, the OCT system was used to measure the time before active tracking responded, either in displacement or signal intensity. Active tracking control lag was measured as the time between when the step and correction started, as observed on OCT at 100 kHz A-scan rate. For anterior lateral lag, a titled pupil phantom was laterally stepped such that lateral tracking error would manifest as OCT axial displacement. This yielded 27.2 ms latency before the galvanometers responded to the step (See FIG. 24). For retinal lateral lag, an eye phantom was laterally stepped with an occlusion at the A-scan position such that lateral tracking error would manifest as increased OCT signal. This yielded 29.8 ms latency before the fast-steering mirror responded to the step (see FIG. 27). For retinal axial lag, an eye phantom was axially stepped such that axial tracking error manifested as OCT axial displacement of the retina. This yielded 24.8 ms latency before the voice coil motor responded to the step (see FIG. 32). This result characterized the anterior scanner as well because axial tracking is performed in the OCT engine which both scanners share. Based on these results, it can be expected to attenuate eye motion at frequencies less than 5.6 Hz laterally and 6.7 Hz axially, which was appropriate for an eye under robot pursuit (see FIG. 33).

Referring to FIG. 33, the figure includes graphs that show pupil alignment error power spectra from all autonomous imaging sessions. The left graph in FIG. 33 shows mean lateral power spectrum of tracked pupil position relative to the scanner once the scanner had grossly aligned. The majority of spectral power is less than the theoretical maximum correction frequency of 5.6 Hz. Gaps in telemetry due to blinks and tracking failures were filled using linear interpolation to enable frequency analysis. The right graph in FIG. 33 shows mean axial power spectrum of tracked pupil position relative to the scanner once the scanner had grossly aligned. The majority of spectral power is less than the theoretical maximum correction frequency of 6.7 Hz. Gaps filled as with the left side graph.

In experiments, initial human testing of the robotic OCT system disclosed herein was tested by using automatic alignment mode. In this mode, the system is under minimal operator control through a pair of foot pedals, which activate automatic alignment and select the target eye. The operator can review the live imaging data as it is collected, switch eyes as desired, and conclude the session once satisfied with the resulting volumes. Five freestanding subjects were imaged this way using the anterior scanner with high (800×800×1376 vx) and intermediate (800×400×1376 vx) density scans (see FIG. 34A, images a-l), requiring approximately 8 s and 4 s to acquire, respectively. In all subjects, OCT volumes were obtained that revealed clinically relevant anatomy of the anterior segment (image d of FIG. 34A) with residual motion artifacts readily corrected in post-processing.

Images a and b of FIG. 34A show right and left 800×800×1376 vx anterior segment volumes obtained with automatic OCT imaging and registration in post-processing. Images c and d of FIG. 34A show corresponding right and left anterior segment un-averaged B-scans from the same subject, revealing contact lens wear and relevant ocular anatomy. Scale bars are 1 mm. Images e-l of FIG. 34A show right and left anterior segment un-averaged B-scans obtained with automatic OCT imaging from four additional subjects, demonstrating reproducibility across subjects. Scale bars are 1 mm.

Image m show in FIG. 34B shows sequential anterior segment 800×400×1376 vx volumes without registration during transient suspension of axial tracking for $t_1<t<t_2$ (gray) and lateral tracking for $t_3<t<t_4$ (gray). Loss of either active tracking dimension produces significant disturbance in the raw data, as compared to the fully tracked volumes, B, artifact from blink; A, axial tracking; L, lateral tracking; T, resumed this volume; ↓, suspended this volume. Image n shown in FIG. 34C shows axial shift required to register each volume from image m, demonstrating increased axial motion artifact only for $t_1<t<t_2$ (gray) when axial tracking is suspended. Mean shift from volumes 4-8 taken as background. Image o in FIG. 34C shows lateral shift required to register each volume from image m, demonstrating increased lateral motion artifact only for $t_3<t<t_4$ (gray) when lateral tracking is suspended. Mean shift from volumes 1-4 and 8 taken as background. Images p-q in FIG. 34C show axial and lateral alignment error from pupil tracking that aligns approximately with images n-o. The physical eye motion correlates with the registration shift during the two tracking suspension periods, revealing the motion stabilization effect of active tracking. B, tracking loss during blink.

To explore the effect of active tracking on volumetric OCT dataset acquisitions, we transiently suspended axial and lateral tracking during anterior imaging of one freestanding subject (image m of FIG. 34A). Anterior instead of retinal imaging was chosen because lateral motion is more readily discerned. Immediately once axial tracking was suspended ($t_1$ in volume 1), we observed significant axial motion artifact. The effect is especially pronounced in volume 2 where the axial motion arises from an interaction between the subject's sway towards and away from the scanner while the robot alone attempts to compensate. When axial tracking is resumed ($t_2$ in volume 3), the motion artifact is immediately suppressed and a largely motion-free volume is obtained. The same sequence of effects was observed when lateral tracking was paused ($t_3$ in volume 5). Volume 6, where no lateral tracking was present, exhibits artifactual distortion of the pupil's circular shape due to lateral motion, as compared to fully tracked volume 4. Again, lateral motion is attenuated when tracking is resumed ($t_4$ in volume 7).

The above qualitative observations were investigated in active tracking telemetry and residual motion estimates recovered from the corresponding OCT data. Lateral and axial shift required to achieve registration in post-processing is a suitable metric to estimate residual motion because a motion-free volume should require little registration. To compensate for registration shift induced by the normal corneal shape, we took the mean per-B-scan shift across all volumes in the dimensions that were tracked as a baseline shift. The axial and lateral shifts (See images n-o) exhibit significant signal primarily when active tracking was suspended (gray regions, approximately). Furthermore, when we aligned the pupil tracking telemetry with the registration shifts, we observed that the registration shifts recapitulate pupil motion waveforms when active tracking is suspended. Although not identical due to blinks and lost A-scans due to scanner flyback between volumes, the similarity of the registration shifts and tracking telemetry indicates that active tracking is effective in eliminating large motion artifact.

To eliminate the operator entirely, a fully autonomous controller was implemented for an experimental robotic OCT system. Unlike automatic imaging where an operator uses foot pedals to trigger imaging, autonomous imaging requires no operator intervention. The controller detects the subject, issues audio prompts for workspace positioning, performs imaging of both eyes for a configurable duration, and dismisses the subject when done. With this controller, five freestanding subjects were autonomously imaged each using the anterior and retinal scanners at 10 s per eye using a low density scan (800×200×1376 vx) requiring approximately 2 s to acquire (i.e., 5 volumes per eye). For the anterior scanner, no per-subject configuration was performed; the system was initiated, the subject was asked to approach, and did not intervene except to close the controller once it announced completion. For the retinal scanner, the scanner was manually adjusted to account for the defocus and length of each subject's eye before commencing autonomous operation. The retinal imaging sessions were otherwise conducted identically to the anterior ones. Notably, retinal imaging was performed without pharmacologic pupil dilation and with ambient overhead lighting.

As with automatic imaging, the autonomous controller obtained anterior segment volumes (see images a and c of FIG. 35A) with attenuated motion artifact which revealed the same anatomic structures of interest as in image d of FIG. 35B. The total interaction time (from subject entrance to exit) for all imaging sessions 50 or less, and the controller maintained imaging for 10 per eye, recovering from initial tracking difficulties with subject (see image b of FIG. 35A). Similarly, autonomous retinal imaging yielded motion stabilized volumes of all subjects' foveas (see images a and c of FIG. 35A) with small residual motion. Although some vignetting and tilt was present, especially in subjects 1 and 2, these volumes revealed the foveal pit, the surrounding parafoveal region, and large retinal vessels. The striping artifact seen in most volumes was due to slight tilting of adjacent B-scans that translation-only registration could not correct. In B-scans through the macula (see image d of FIG. 35C), major retinal tissue layers and the underlying choroid were identified. As with anterior imaging, total interaction time was again under 50 for all subjects (see image b of FIG. 35A).

Images a and c of FIG. 35A show right and left 800× 200×1376 vx anterior segment volumes obtained with fully autonomous OCT imaging and registration in post-processing. These scans capture the full cornea and iris surfaces, except those portions which the superior eyelid covers. Eyelashes are seen facing towards the eye in some volumes due to their large axial extent that produces wraparound OCT artifacts. Image b of FIG. 35A show autonomous system mode from initial to last subject detection. For all subjects, the system reliably performs 10 s of imaging per eye after aligning with the right and then the left eye for a total session time of under 60 s. Moreover, the system recovers from eye tracking loss, as seen with the second subject, and subsequently images for an uninterrupted 10 s. Image d of FIG. 35C show unaveraged B-scans for each subject, revealing the cornea, anterior chamber, iris, angle of cornea, and pupil. Scale bars are 1 mm.

In addition, the quality of these OCT volumes were obtained autonomously. For anterior volumes, we measured the central corneal thickness (CCT) and anterior chamber depth (ACD) with index correction and compared them to published values for these parameters. For retinal volumes, an unaffiliated, expert reviewer evaluated the gradability of B-scans through the fovea. Gradability is commonly assessed before subjecting a B-scan to thorough analysis for signs of retinal disease. The mean parafoveal retinal thickness (PRT) was measured and compared to previously published values. In each case, one B-scan was selected from each eye of each subject, yielding a total of ten anterior segment and retinal B-scans each for analysis. B-scans were selected from volumes to avoid artifact from tilt, which the system was not designed to correct, and blinking. The expert reviewer rated all selected retinal B-scans as appropriate for grading, indicating they met the quality standards necessary for disease evaluation. Anterior segment measurements yielded a mean CCT of 0.539 mm (range 0.504-0.585 mm) and mean ACD of 3.784 mm (range 3.054-4.199 mm). For retinal imaging, we measured a PRT of 250 µm (range 215-3084 These results were consistent with prior studies reporting CCT, ACD, and PRT in healthy normal eyes, like those of our subjects, and the general population.

FIG. 36 shows images of autonomous retinal imaging results in freestanding subjects with undilated eyes. Images a and c of FIG. 36 show right and left 800×200×1376 vx retinal volumes obtained with fully autonomous OCT imaging and registration in post-processing. These scans penetrate all retinal layers into the choroid and reveal the foveal pit within the surrounding parafoveal region. Volumes are axially stretched by a factor of two to reveal structure. See FIG. 37 for raw volumes. B, artifact from blink. Image b of FIG. 36 shows autonomous system mode from initial to last subject detection. For all subjects, the system reliably performs 10 s of imaging per eye after aligning with the right and then the left eye with a total session time of under 60 s. The time required in advance to manually adjust the scanner for each subject's eye defocus and length is not included. Image d of FIG. 36 shows unaveraged B-scans through the fovea for each subject, revealing the fovea centralis, constituent retinal layers, and underlying choroid. B-scans are axially stretched by a factor of three to reveal structure. Scale bars are 250 µm laterally.

In experiments, scanner optical design was performed in OpticStudio (Zemax) using 1000 nm, 1050 nm, and 1100 nm wavelengths over the 3×3 matrix of configurations shown in FIGS. 17 and 18. We used the Navarro eye model for retinal scanner optical optimization. The design used 2 B-coated achromatic doublets (Thorlabs) with 200 mm focal lengths for the objective and relay lens pairs in both scanners. Galvanometers (Saturn 1B galvanometer available from ScannerMax) were used to scan the OCT A-scan. Short-pass dichroics inserted the OCT beam path over the inline pupil camera's field of view. The retinal scanner used a 2×3 inch fast steering mirror (OIM202.3 steering mirror available from Optics in Motion) with 3° angular range for pupil pivot adjustment. Scanner mechanical design was performed in Inventor software (available from Autodesk) according to the optical optimization results. The scanners were rendered from 3D printed plastic parts derived from the mechanical models. Active tracking relied on three Blackfly S monochrome cameras (BFS-U3-042M, FLIR Systems) operating at 350 Hz. The left and right camera poses were calibrated in the inline camera's coordinate frame using chessboard calibration targets. Each camera was initialized using OpenCV stereo calibration, and then all camera parameters were refined with bundle adjustment. The pupil in each camera view was detected in parallel using custom C++ software that identified dark circles. The pupil position in 3D space was estimated through linear triangulation when at least two cameras reported pupil presence. To facilitate pupil detection, each scanner included an infrared illumination ring, using 850 nm light for the anterior scanner and 720 nm light for the retinal scanner. The cameras were fitted with filters to reject the OCT light. For scan aiming, the galvanometer and FSM were calibrated to the inline pupil camera by sweeping the OCT A-scan across the sample plane at the working distance while the camera filters were temporarily removed. The scan spot was detected in custom Python software and performed linear regression to map galvanometer/FSM drive commands to physical position. For anterior active tracking, the OCT scan waveform was adjusted using a summing amplifier inserted before the input of each galvanometer axis. For retinal active tracking, we interfaced with the FSM directly.

For tracking accuracy and precision, pupil tracking telemetry was recorded at 350 while a paper eye phantom was moved on a motorized stage (A-LSQ150D-E01, Zaber) with 4 µm repeatability and 100 µm accuracy. The paper eye phantom consisted of a black circle on a white background to satisfy the pupil tracking algorithm. Starting with the phantom grossly aligned with the scanner's optical axis at the working distance, we advanced the stage in 1 mm steps five times forward, ten times reverse, and five times forward. The experiment was performed axially and laterally, and yielded 21 total position measurements for each dimension. To estimate accuracy, the commanded stage position was subtracted from the mean of each of these recordings and computed the RMS value. To estimate precision, the mean of each recording was subtracted from itself and computed the RMS value across all recordings together.

For latency, the OCT system was used to measure the active tracking response because the goal of active tracking is to stabilize the OCT A-scan against motion. Moreover, this approach gave 10 µs temporal and 5 µm spatial resolution. The OCT system was used to acquire successive A-scans without scanning the beam so that only active tracking affected the scan location. To measure axial latency, a retinal eye phantom (Rowe Eye, Rowe Technical Design) was mounted on a motorized stage (A-LSQ150D-E01, Zaber) and rapidly stepped the stage 1 mm axially. Axial tracking error was read from the A-scan data by registering adjacent A-scans using cross-correlation. The same procedure with a 2 mm step was applied for anterior lateral latency where the tilted paper eye phantom's lateral motion produced axial displacement on OCT. To measure retinal lateral latency, a spot occlusion was placed on the retinal eye phantom, adjusted active tracking to position the scan on the occlusion, and rapidly stepped the phantom laterally 2 mm. When the OCT beam was blocked by the occlusion, the resulting A-scan had low intensity and high intensity otherwise. Thus, active tracking was characterized by its ability to hold the beam on the occlusion, producing a low intensity A-scan. Brightness was read out using the maximum intensity from the A-scan data of an OCT acquisition during the lateral step. In all latency measurements, the elapsed time between when the stage motion started and when the relative stage motion reversed direction was used.

Robotic scanner positioning for automatic and autonomous imaging used a stepwise approach for obtaining eye images. The controller used two 3D cameras (RealSense D415, Intel) positioned to view the imaging workspace from the left and from the right. Facial landmarks in the cameras' infrared images were detected using OpenFace 2.0 and extracted the left and right eye positions in 3D space from the corresponding point clouds at approximately 30 Hz, subject to image processing times. During the initial "position" stage, the controller held the scanner in a recovery position that prevented occlusion of the imaging workspace and waited to identify a face. During the "align" stage, the controller grossly aligned the scanner with the target eye based on face tracking results. This motion was performed open-loop without any scanner-based feedback. Eye positions were consequently smoothed with a -sample moving average filter (approximately 200 ms) to reduce noise in the target position. In automatic imaging, the controller only entered the "align" stage when the operator depressed the enabling foot pedal. In autonomous imaging, however, the controller entered the "align" stage once a face had been continuously detected for a preset time.

Once the scanner detected the pupil, the controller entered the "image" stage in which it finely aligned the scanner's optical axis with the eye using pupil tracking results. OCT images were considered as valid during this stage. These fine alignment motions were performed closed-loop with a proportional control that eliminated the pupil alignment error. Face tracking results continued to be used as a consistency check but not for servoing. In automatic imaging, the controller remained in the "image" stage until the operator released the foot pedal or the scanner reported a pupil tracking loss. In autonomous imaging, the controller returned to the "align" to image the next eye or entered the "done" stage after the preset imaging time had elapsed. The controller issued voice prompts during each stage to facilitate alignment and inform subjects of its actions. A UR3 collaborative robot arm (Universal Robots) was used for manipulating the scanner, which the controller commanded at 125 Hz. The controller downsampled the pupil tracking results from 350 Hz to 125 Hz by dropping outdated samples.

OCT data was recorded from the balanced receiver using a 1.8 GS/s A/D card (ATS9360, AlazarTech) and processed using custom C++ software with graphics processing unit (GPU) acceleration. The raw data was processed according to standard frequency domain OCT techniques (e.g., inverse discrete Fourier transform, DC subtract, etc.), and the resulting volumes were saved in log-scale. B-scans were generated from the log-scale volumes by rescaling based on chosen black and white thresholds. Identical thresholds were used for all anterior segment B-scans and for all retinal B-scans. In addition, retinal B-scans were cropped to remove scan flyback artifacts and empty space; the same cropping was used for all retinal B-scans. Volumetric images were generated using direct volume rendering implemented in custom Python and C++ software with GPU acceleration. Volumes were thresholded, rescaled, 3×3×3 median filtered, and Gaussian smoothed along the axial and fast scan dimensions before raycasting. All volumetric renders used the same pipeline and parameters, except for variation in the threshold, render angle, and axial scale between anterior segment and retinal volumes. As with B-scans, an identical threshold was applied to all anterior segment volumes and applied to all retinal volumes. We performed registration in post-processing according to the peak cross-correlation of adjacent B-scans laterally and axially. The cross-correlation signal was filtered to reject large shifts (e.g., blinks) and applied Gaussian smoothing to eliminate low-amplitude noise. Volumes were also cropped to remove scan flyback and lens reflection artifacts, with the same copping applied to all anterior segment and to all retinal volumes.

In accordance with embodiments, subsequent to pupil identification, the system can enter a gaze tracking mode. To perform gaze tracking, corneal reflections from a suitable light source (e.g., 4 LEDs in an illumination ring) may be detected. If the system detects at least 3 reflections per camera in at least 2 pupil cameras, it enters gaze tracking and calculates the center of corneal curvature, the optical axis, and visual axis of the eye. For each combination of light source and camera, a plane can be defined with 3 points: the camera lens center, the center of the corneal reflection image formed at the camera sensor, and the light source location. The center of corneal curvature can be calculated as the intersection between all of the planes. The optical axis can be defined as the axis between the center of corneal reflection and the pupil center point. The visual axis can be calculated by rotating the optical axis by two angular offsets: one horizontal and one vertical. These angular offsets are calibrated for each subject before imaging. From the visual axis and the OCT system's optical axis, a difference in two angles, pan and tilt, can be measured and communicated to the robot control software.

The present subject matter may be a system, a method, and/or a computer program product. The computer program product may include a computer readable storage medium (or media) having computer readable program instructions thereon for causing a processor to carry out aspects of the present subject matter.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a RAM, a ROM, an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network, or Near Field Communication. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present subject matter may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++, Javascript or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present subject matter.

Aspects of the present subject matter are described herein with reference to flowchart illustrations and/or block diagrams of methods, apparatus (systems), and computer program products according to embodiments of the subject matter. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present subject matter. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the embodiments have been described in connection with the various embodiments of the various figures, it is to be understood that other similar embodiments may be used, or modifications and additions may be made to the described embodiment for performing the same function without deviating therefrom. Therefore, the disclosed embodiments should not be limited to any single embodiment, but rather should be construed in breadth and scope in accordance with the appended claims.

What is claimed is:

1. A system comprising:
   a scanner configured to image a target feature of a subject;
   a mechanism configured to move the scanner;
   a subject tracker comprising one or more stationary cameras configured to track positioning of the subject;
   a feature tracker comprising one or more cameras disposed on the mechanism and configured to track positioning of the target feature within an area within which the target feature is positioned such that the target feature is imageable by the scanner; and
   a controller configured to:
     control the user interface to present positioning feedback information based on the tracked position of the subject;
     determine whether the subject is positioned within a predetermined position for tracking the target feature;
     control the mechanism to move the feature tracker to a position such that
     the feature tracker is operable to track a position of the target feature based on the tracked position of the subject by the subject tracker in response to determining that the subject is positioned within the predetermined position for tracking the target feature;
     control the mechanism to move the scanner to a position such that the scanner is operable to image the target feature based on the tracked position of the target feature by the feature tracker; and
     control the scanner to image the target feature, the scanner is an optical coherence tomography (OCT) scanner configured to generate one or more images of the target feature of the subject.

2. The system of claim 1, wherein the target feature is an eye of the subject.

3. The system of claim 1, wherein the subject is a face of a person.

4. The system of claim 1, wherein the feature tracker is configured to track a pupil of an eye.

5. The system of claim 1, wherein the target feature is one of a retina of an eye and an anterior segment of an eye of the subject, and wherein the scanner is an OCT scanner; and
   wherein the controller is configured to:
     receive a command to capture an OCT image of the target feature; and
     control the OCT scanner to capture the OCT image of the target feature subsequent to the OCT scanner being positioned such that the OCT scanner is operable to image the eye.

6. The system of claim 5, wherein the controller is configured to implement the functions of controlling the mechanism to move the feature tracker and controlling the mechanism to move the scanner in response to receiving the command.

7. The system of claim 1, further comprising a user interface, and wherein the controller is configured to control the user interface to present feedback information to the subject based on the tracked position of the subject.

8. A method comprising:
providing a scanner configured to image a target feature of a subject;
providing a mechanism configured to move the scanner;
tracking a position of the subject having the target feature for imaging using one or more stationary cameras;
using a feature tracker comprising one or more cameras disposed on the mechanism, wherein the feature tracker is configured to track positioning of the target feature within an area within which the target feature is positioned such that the target feature is imageable by the scanner;
controlling a user interface to present positioning feedback information based on the tracked position of the subject;
determining whether the subject is positioned within a predetermined position for tracking the target feature;
controlling a mechanism to move a feature tracker to a position such that the feature tracker is operable to track a position of the target feature of the subject based on the tracked position of the subject in response to determining that the subject is positioned within the predetermined position for tracking the target feature;
controlling the mechanism to move a scanner to a position such that the scanner is operable to image the target feature based on the tracked position of the target feature by the feature tracker; and
controlling the scanner to image the target feature, the scanner is an optical coherence tomography (OCT) scanner configured to generate one or more images of the target feature of the subject.

9. The method of claim 8, wherein the target feature is an eye of the subject.

10. The method of claim 8, wherein the subject is a face of a person.

11. The method of claim 8, wherein the feature tracker is configured to track a pupil of an eye.

12. The method of claim 8, wherein the target feature is one of a retina of an eye and an anterior segment of an eye of the subject, and wherein the scanner is an OCT scanner; and
wherein the method further comprises:
receiving a command to capture an OCT image of the target feature; and
controlling the OCT scanner to capture the OCT image of the target feature subsequent to the OCT scanner being positioned such that the OCT scanner is operable to image the eye.

13. The method of claim 12, wherein the steps of controlling the mechanism to move the feature tracker and controlling the mechanism to move the scanner are implemented in response to the step of receiving the command.

14. The method of claim 7, wherein the feature tracker comprises one or more cameras disposed on the mechanism.

15. The method of claim 8, further comprising a user interface, and
wherein the method further comprises controlling the user interface to present feedback information to the subject based on the tracked position of the subject.

* * * * *